United States Patent
Barbas, III et al.

(10) Patent No.: US 6,346,249 B1
(45) Date of Patent: Feb. 12, 2002

(54) METHODS FOR REDUCING THE EFFECTS OF CANCERS THAT EXPRESS A33 ANTIGEN USING A33 ANTIGEN SPECIFIC IMMUNOGLOBULIN PRODUCTS

(75) Inventors: Carlos F. Barbas, III, Solana Beach; Christoph Rader, San Diego, both of CA (US); Gerd Ritter, New York, NY (US); Sydney Welt, New York, NY (US); Lloyd J. Old, New York, NY (US)

(73) Assignees: Ludwig Institute for Cancer Research, New York, NY (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/543,004

(22) Filed: Apr. 4, 2000

Related U.S. Application Data

(63) Continuation-in-part of application No. 09/425,638, filed on Oct. 22, 1999.

(51) Int. Cl.$^7$ ............................................. A61K 39/395
(52) U.S. Cl. .................. 424/181.1; 424/130.1; 424/156.1; 424/183.1; 530/388.8; 530/388.85; 530/389.7
(58) Field of Search ................ 424/130.1, 133.1, 424/134.1, 135.1, 155.1, 156.1, 178.1, 183.1, 181.1; 530/387.1, 387.3, 388.1, 388.8, 388.85, 389.1, 389.7, 391.3, 391.7

(56) References Cited

U.S. PATENT DOCUMENTS

| | | |
|---|---|---|
| 4,675,187 A | 6/1987 | Konishi et al. |
| 4,704,692 A | 11/1987 | Ladner |
| 5,160,723 A | 11/1992 | Welt et al. |
| 5,585,089 A | 12/1996 | Queen et al. |
| 5,643,550 A | 7/1997 | Welt et al. |
| 5,712,369 A | 1/1998 | Old et al. |
| 5,952,484 A | 9/1999 | Wallace et al. |
| 5,958,412 A | 9/1999 | Welt et al. |

FOREIGN PATENT DOCUMENTS

| | | |
|---|---|---|
| EP | 120694 | 10/1984 |
| EP | 125023 | 11/1984 |
| GB | 2188638 | 10/1987 |
| WO | WO 91/09967 | * 7/1991 |

OTHER PUBLICATIONS

Jian, Scientific American 271:58, 1994.*
Chatterjee et al., Cancer Immunol. Immunother. 38:75–82, 1994.*
Gura, Science 278:1041–42, 1997.*
Groves et al., Hybridoma 6:71–76, 1987.*
Panka et al., Proc. Natl. Acad. Sci. USA 85:3080–84, 1988.*
Rudikoff et al., Proc. Natl. Acad. Sci. USA 79:1979–83, 1982.*
Amit et al., Science 233:747–753, 1986.*
Seaver., Genetic Engineering News 14:10 and 21, 1994.*
Schroff, et al., Canc. Res. 45:879–885 (1985).
Bruggemann, et al., J. Exp. Med 170:2153–2157 (1989).
Riechmann, et al., Nature 332:323–327 (1988).
Vaughan, et al., Nat. Biotechnol. 16(6):535–539 (1998).
Knight, et al., Adv. Immunol 56:179–218 (1994).
Dayhoff et al., Meth. Enzymol., 91:524–545 (1983).
Williams and Barclay, in Immunglobulin Genes, p 361, Academic Press, NY (1989).
Bird et al., Science, 242:423–426 (1988).
Old, L.J. Immunotherapy for Cancer, Scientific American, Sep. 1996.
Ulrich et al., Proc. Natl. Acad Sci USA 92(25):11907–11 (1995).
Rader, et al., Proc. Natl. Acad Sci USA 95:(15):8910–8915 (1998).
deWildt, et al., J. Mol. Biol 285(3):895–901 (1999).
Presta, et al., Canc. Res. 57(20):4593–9 (1997).
Moritz, R.L. et al., J. Chromatogr. A, 798:91–101, 1998.
(Pfreundschuh, M. et al., Proc. Natl. Acad. Sci. (Wash.), 75, 5122–5126 (1978)).
Catimel, B. et al., J. Biol. Chem. 271:25664–25670), 1996.

* cited by examiner

Primary Examiner—Sheela Huff
Assistant Examiner—Larry R. Helms
(74) Attorney, Agent, or Firm—Fulbright & Jaworski, LLP

(57) ABSTRACT

The invention is directed to methods of reducing the effects of cancer in a subject by administering to said subject a pharmaceutically effective amount of an anti-cancer agent conjugated to an inmmunoglobulin product which comprises one or more novel complementarity determining region and framework regions.

19 Claims, 10 Drawing Sheets

```
              VL-FR1                    VL-CDR1        VL-FR2            VL-CDR2    VL-FR3                                    VL-CDR3      VL-FR4
              1                      23  24    34 35                49  50    56 57                                       88 89       95ab97 98      107
rabbit VL1    EFDMTQTPPSLSASVGETVRIRC LASEFLFNGVS WYQQKPGKPPKFLIS GASNLES GVPPRFSGSGSGSGTDYTLTIGGVQAEDVATYYC LGGYSGSSSGLT FGAGTNVEIK  (SEQ ID NO:20)
rabbit VL2    ELVMTQTPPSLSASVGETVRIRC LASDPLFNGVS WYQQKPGKPPKFLIS GASNLES GVPPRFSGSGSGSGTDYTLTIGGVQAEDVATYYC LGGYSGSSSGLT FGAGTNVEIK  (SEQ ID NO:21)
rabbit VL3    ELVLTQTPPSLSASVGETVRIRC LASDPLFNGVS WYQQKPEKPPTFLIS GASDLET GVPPRFSGSGSGSCTDYTLTIGGVQAEDAATYYC LGGYSGSSAGLT FGAGTNVEIK  (SEQ ID NO:22)
Hum lib VL    ELQMTQSPSSLSASVGDRVRITC LASEFLFNGVS WYQQKPGKAPKFLIY GASNLES GVPPRFSGSGSGTDFTLTISSLQPEDVATYYC LGGYSGSSSGLT FGGGTKVEIK  (SEQ ID NO:45)
                                                                                                 Y                A
Human VLA     ELQMTQSPSSLSASVGDRVRITC LASEFLFNGVS WYQQKPGKAPKFLIY GASNLES GVPPRFSGSGSGTDYTLTISSLQPEDVATYYC LGGYSGSSSGLT FGGGTKVEIK  (SEQ ID NO:39)
Human VLB     ELQMTQSPSSLSASVGDRVRITC LASEFLFNGVS WYQQKPGKVPKFLIY GASNLES GVPPRFSGSGSGTDFTLTISSLQPEDVATYYC LGGYSGSSSGLT FGGGTKVEIK  (SEQ ID NO:40)
Human VLC     ELQMTQSPSSLSASVGDRVRITC LASEFLFNGVS WYQQKPGKVPKFLIY GASNLES GVPPRFSGSGSGTDFTLTISSLQPEDVATYYC LGGYSGSSSGLT FGGGTKVEIK  (SEQ ID NO:41)
Human VLD     ELQMTQSPSSLSASVGDRVRITC LASEFLFNGVS WYQQKPGKAPKFLIY GASNLES GVPPRFSGSGSGTDYTLTISSLQPEDVATYYC LGGYSGSSSGLT FGGGTKVEIK  (SEQ ID NO:42)
Human VLE     ELQMTQSPSSLSASVGDRVRITC LASEFLFNGVS WYQQKPGKAPKFLIY GASNLES GVPPRFSGSGSGTDFTLTISSLQPEDVATYYC LGGYSGSSSGLT FGGGTKVEIK  (SEQ ID NO:43)
Human VLF     ELQMTQSPSSLSASVGDRVRITC LASEFLFNGVS WYQQKPGKAPKFLIY GASNLES GVPPRFSGSGSGTDFTLTISSLQPEDVATYYC LGGYSGSSSGLT FGGGTKVEIK  (SEQ ID NO:44)
                                                                        V F
```

VH

```
              VH-FR1                           VH-CDR1    VH-FR2            VH-CDR2                    VH-FR3                                VH-CDR3            VH-FR4
              1                             30 31 35 36            49  50 52a      57                65 66                         82abc 94 95 100abcdefg 103        113
rabbit VH1    QQQVMESGGGLVTLGGSLTLTCKASGIDFS NNGIS WVRQAPGKGLEWIL YIYPDYGSTDYGST TITPNYGSVDYASSVNG RFTISLDNAQNTVFLQMTSLTAADTATYFCAR DRGAYAGSRGTRLDL WGQGTLVTVSS  (SEQ ID NO:46)
rabbit VH2    QEQLMESGGGLVTLGGSLKLSCAASGIDFS HYGIS WVRQAPGKGLEWIA YIYPNYGSVDYASSVNG TITPNYGSVDYASSVNG RFTISLDNAQNTVFLQMISLTAADTATYFCAR DRGYYSGSRGTRLDL WGQGTLVTVSS  (SEQ ID NO:47)
rabbit VH3    QEQVMESGGGLVTLGGSLKLSCAASGIDFS HYGIS WVRQAPGKGLEWIA YIYPNYGSVDYASSVNG TITPNYGSVDYASSVNG RFTISLDNAQNTVFLQMSLTAADTATYFCAR DRGYYSGSRGTRLDL WGQGTLVTISS  (SEQ ID NO:48)
Hum lib VH    EVQVMESGGGLVKPGGSLRLSCAASGFTPS HYGIS WVRQAPGKGLEWVA YIYPNYGSVDYASSVNG TITPNYGSVDYASSVNG RFTISRDNAKNSLYLQMNSLRAEDTATYYCAR DRGYYSGSRGTRLDL WGQGTLVTVSS  (SEQ ID NO:49)
                                             ID                                                                L  Q  V           F
Human VHA     EVQVMESGGGLVKPGGSLRLSCAASGIGFS HYGIS WVRQAPGKGLEWVS TITPNYGSVDYASSVNG RFTISFDNAQNSLYLQMNSLRAEDTAVYYCAR DRGYYSGSRGTRLDL WGQGTLVTVSS  (SEQ ID NO:50)
Human VHB     EVQVMESGGGLVKPGGSLRLSCAASGIGFS HYGIS WVRQAPGKGLEWVS TITPNYGSVDYASSVNG RFTISRDNAQNSLYLQMNSLRAEDTAVYFCAR DRGYYSGSRGTRLDL WGQGTLVTVSS  (SEQ ID NO:51)
Human VHC     EVQVMESGGGLVKPGGSLRLSCAASGIGFS HYGIS WVRQAPGKGLEWVS TITPNYGSVDYASSVNG RFTISLDNAQNSLYLQMNSLRAEDTAVYFCAR DRGYYSGSRGTRLDL WGQGTLVTVSS  (SEQ ID NO:52)
Human VHD     EVQVMESGGGLVKPGGSLRLSCAASGIGFS HYGIS WVRQAPGKGLEWVS TITPNYGSVDYASSVNG RFTISRDNAKNSLYLQMNSLRAEDTAVYFCAR DRGYYSGSRGTRLDL WGQGTLVTVSS  (SEQ ID NO:53)
Human VHE     EVQVMESGGGLVKPGGSLRLSCAASGIGFS HYGIS WVRQAPGKGLEWVS TITPNYGSVDYASSVNG RFTISRDNAKNSLYLQMNSLRAEDTAVYFCAR DRGYYSGSRGTRLDL WGQGTLVTVSS  (SEQ ID NO:54)
Human VHF     EVQVMESGGGLVKPGGSLRLSCAASGIGFS HYGIS WVRQAPGKGLEWVS TITPNYGSVDYASSVNG RFTISLDNAQNSLYLQMNSLRAEDTAVYFCAR DRGYYSGSRGTRLDL WGQGTLVTVSS  (SEQ ID NO:55)
Human VHG     EVQVMESGGGLVKPGGSLRLSCAASGIGFS HYGIS WVRQAPGKGLEWVS TITPNYGSVDYASSVNG RFTISRDNAKNSLYLQMNSLRAEDTAVYYCAR DRGYYSGSRGTRLDL WGQGTLVTVSS  (SEQ ID NO:56)
Human VHH     EVQVMESGGGLVKPGGSLRLSCAASGIGFS HYGIS WVRQAPGKGLEWVS TITPNYGSVDYASSVNG RFTISRDNAKNSLYLQMNSLRAEDTAVYYCAR DRGYYSGSRGTRLDL WGQGTLVTVSS  (SEQ ID NO:57)
Human VHI     EVQVMESGGGLVKPGGSLRLSCAASGIGFS HYGIS WVRQAPGKGLEWVS TITPNYGSVDYASSVNG RFTISLDNAQNSLYLQMNSLRAEDTAVYYCAR DRGYYSGSRGTRLDL WGQGTLVTVSS  (SEQ ID NO:58)
Human VHJ     EVQVMESGGGLVKPGGSLRLSCAASGIGFS HYGIS WVRQAPGKGLEWVS TITPNYGSVDYASSVNG RFTISLDNAQNSLYLQMNSLRAEDTAVYYCAR DRGYYSGSRGTRLDL WGQGTLVTVSS  (SEQ ID NO:59)
Human VHK     EVQVMESGGGLVKPGGSLRLSCAASGIGFS HYGIS WVRQAPGKGLEWVS TITPNYGSVDYASSVNG RFTISLDNAQNSLYLQMNSLRAEDTAVYYCAR DRGYYSGSRGTRLDL WGQGTLVTVSS  (SEQ ID NO:60)
Human VHL     EVQVMESGGGLVKPGGSLRLSCAASGIGFS HYGIS WVRQAPGKGLEWVS TITPNYGSVDYASSVNG RFTISLDNAQNSLYLQMNSLRAEDTAVYYCAR DRGYYSGSRGTRLDL WGQGTLVTVSS  (SEQ ID NO:61)
Human VHM     EVQVMESGGGLVKPGGSLRLSCAASGIGFS HYGIS WVRQAPGKGLEWVS TITPNYGSVDYASSVNG RFTISSDNAQNSLYLQMNSLRAEDTAVYYCAR DRGYYSGSRGTRLDL WGQGTLVTVSS  (SEQ ID NO:62)
Human VHN     EVQVMESGGGLVKPGGSLRLSCAASGIGFS HYGIS WVRQAPGKGLEWVS TITPNYGSVDYASSVNG RFTISSDNAQNSLYLQMNSLRAEDTAVYYCAR DRGYYSGSRGTRLDL WGQGTLVTVSS  (SEQ ID NO:63)
Human VHO     EVQVMESGGGLVKPGGSLRLSCAASGIGFS HYGIS WVRQAPGKGLEWVS TITPNYGSVDYASSVNG RFTISSDNAQNSLYLQMNSLRAEDTAVYYCAR DRGYYSGSRGTRLDL WGQGTLVTVSS  (SEQ ID NO:64)
Human VHP     EVQVMESGGGLVKPGGSLRLSCAASGIGFS HYGIS WVRQAPGKGLEWVS TITPNYGSVDYASSVNG RFTISSDNAQNSLYLQMNSLRAEDTAVYYCAR DRGYYSGSRGTRLDL WGQGTLVTVSS  (SEQ ID NO:65)
Human VHQ     EVQVMESGGGLVKPGGSLRLSCAASGIGFS HYGIS WVRQAPGKGLEWVS TITPNYGSVDYASSVNG RFTISSDNAQNSLYLQMNSLRAEDTAVYYCAR DRGYYSGSRGTRLDL WGQGTLVTVSS  (SEQ ID NO:66)
Human VHR     EVQVMESGGGLVKPGGSLRLSCAASGIGFS HYGIS WVRQAPGKGLEWVS TITPNYGSVDYASSVNG RFTISSDNAQNSLYLQMNSLRAEDTAVYYCAR DRGYYSGSRGTRLDL WGQGTLVTVSS  (SEQ ID NO:67)
```

FIG. 4

Mixed hemadsorption titer (ng/ml)

| Clone | | LIM1215 | SW1222 | HT29 | SW620 |
|---|---|---|---|---|---|
| human Fab | A | 10* | 1 | nd | nd |
| | B | 10 | 5 | nd | nd |
| | E | 40 | 20 | nd | nd |
| | F | 10 | 20 | nd | nd |
| human IgG A33 | | 5 | 5 | nd | nd |

…

METHODS FOR REDUCING THE EFFECTS OF CANCERS THAT EXPRESS A33 ANTIGEN USING A33 ANTIGEN SPECIFIC IMMUNOGLOBULIN PRODUCTS

RELATED APPLICATIONS

This application is a continuation-in-part application of U.S. Ser. No. 09/425,638 filed Oct. 22, 1999, which is hereby incorporated by reference.

This application was made with government support under Contract AI41944 by the National Institutes of Health. The government has certain rights in the invention.

FIELD OF THE INVENTION

This invention relates to immunoglobulin products that bind with specificity to A33 antigen. In particular this invention is directed to A33 antigen specific CDRs. The antibodies and antibody like proteins may be humanized.

BACKGROUND AND PRIOR ART

Use of antibodies as therapeutic agents is gaining acceptance as an important and valuable approach in the treatment of various conditions, such as types of cancer. The specificity of antibodies makes them particularly useful in treating conditions where a "marker" or "markers" characterize abnormal cells. Antibodies effectively target such cells by binding to these markers, which are molecules present in, or preferably on, the cell type of interest.

Initial forays into the production of antibodies used mice as subject animals. To summarize, mice were injected with the molecule of interest. As this molecule was foreign to the mouse, an antibody response would result. The antibodies were then purified from murine blood or serum, for eventual diagnostic or therapeutic use.

In vivo use of murine antibodies has been curtailed, however, for a number of reasons. Murine antibodies, recognized as foreign by a human host, elicit the so-called "human anti-mouse antibody" or "HAMA" response. See, e.g., Schiff, et al., Canc. Res. 45:879–885 (1985). In addition, the Fc portion of murine antibodies is not as efficacious in stimulating human complement or cell mediated toxicity.

There have been extensive and intensive efforts to circumvent such problems. One such approach is the development of chimeric antibodies. See, e.g., European Patent Applications 120694 and 125023 disclosing the general approach. Chimeric antibodies contain portions of antibodies from two or more different species, such as the variable regions of a mouse antibody, and the constant regions of a human antibody. The advantage of such chimeras is that they retain the specificity of murine antibodies, but also stimulate human Fc complement fixation. Such chimeras can still elicit a HAMA response, however. See, e.g., Bruggemann, et al., J. Exp. Med 170:2153–2157 (1989).

Additional approaches have been sought which would alleviate these problems. British Patent Application GB 2188638A and U.S. Pat. No. 5,585,089 are exemplary of technology in this area. These references disclose processes wherein recombinant antibodies are produced where the only portion of the antibody that is substituted is the complementarity determining region, or "CDR." The CDR grafting technique has been used to generate antibodies which consist of murine CDRs, and human variable region framework and constant regions. See, e.g., Riechmann, et al., Nature 332:323–327 (1988), for teachings relating to such "humanized" antibodies. These antibodies retain the human constant regions that are necessary for Fc dependent effector function, but are much less likely to evoke a HAMA response.

Substitution of murine CDRs for human CDRs is not generally sufficient to generate an efficacies humanized antibody. The humanized antibodies must include a small number of critical murine antibody residues in the human variable region. The particular residues of importance depend upon the structure of both the murine antibody and human antibody. See, e.g., WO 04381 to Harris et al. (2000).

Notwithstanding these issues, humanized antibodies have become much more available, as is evidenced by, e.g., U.S. Pat. No. 5,952,484 to Wallace et al. and U.S. Pat. No. 5,958,412 to Welt et al., both of which are incorporated by reference.

U.S. Pat. No. 5,958,412 describes humanized antibodies to a molecule referred to as "A33." This molecule is known to be associated with colon cancer. See, e.g., U.S. Pat. Nos. 5,643,550 and 5,160,723, incorporated by reference. Also see U.S. Pat. No. 5,712,369, to Old, et al., also incorporated by reference, teaching the isolation and characterization of the A33 molecule.

Phage display is a methodology which has been used to express and to select recombinant antibodies. See, e.g., Vaughan, et al., Nat. Biotechnol. 16(6):535–539 (1998), incorporated by reference. This methodology is employed in the disclosure which follows.

The rabbit Ig gene repertoire has been well characterized. See, e.g., Knight, et al., Adv. Immunol 56:179–218 (1994). This characterization has permitted selection of monoclonal antibodies, by screening combinatorial antibody libraries displayed on phage (Ridder, et al., Biotechnology95(15):8910–15(1998). This information, together with information discussed infra, has been used to develop the invention described herein.

The structure of an immunoglobulin is discussed in standard textbooks such as Paul, W. E, Fundamental Immunology, Raven Press, New York, N.Y., 1993. Incorporated herein by reference.

BRIEF DESCRIPTION OF THE DRAWINGS

FIG. 1 depicts the amino acid sequence of the V regions of rabbit anti A33 antigen antibodies. In particular, three rabbit antibodies, rabbit 1, rabbit 2 and rabbit 3 are shown. Further, the V sequence of the humanized antibodies is shown. Finally, the amino acid sequence of six human antibodies, labelled human A to F are listed. The framework regions, corresponding to about amino acids 1–22 (FR1), 35–49 (FR2), 57–88 (FR3) and 98–107 (FR4) of the VL chain and amino acids 1–30(FR1), 36–49(FR2),66–94 (FR3),103–113 (FR4) of the VH chain. The CDR regions correspond to about amino acids 24–34 (CDR1), 50–56 (CDR2), 89–97 (CDR3) of the VL chain and about amino acids 31–35 (CDR1), 50–65 (CDR2), and 95–109 (CDR3) of the VH chain.

FIG. 4 depicts the results of affinity measurements on human Fab. Human A refers to human VLA and VHA, Human B refers to human VLB and VHB, Human E refers to human VLE and VHE, Human F refers to human VLF and VHF.

DETAILED DESCRIPTION OF PREFERRED EMBODIMENTS

A. Definitions

Figure 2:
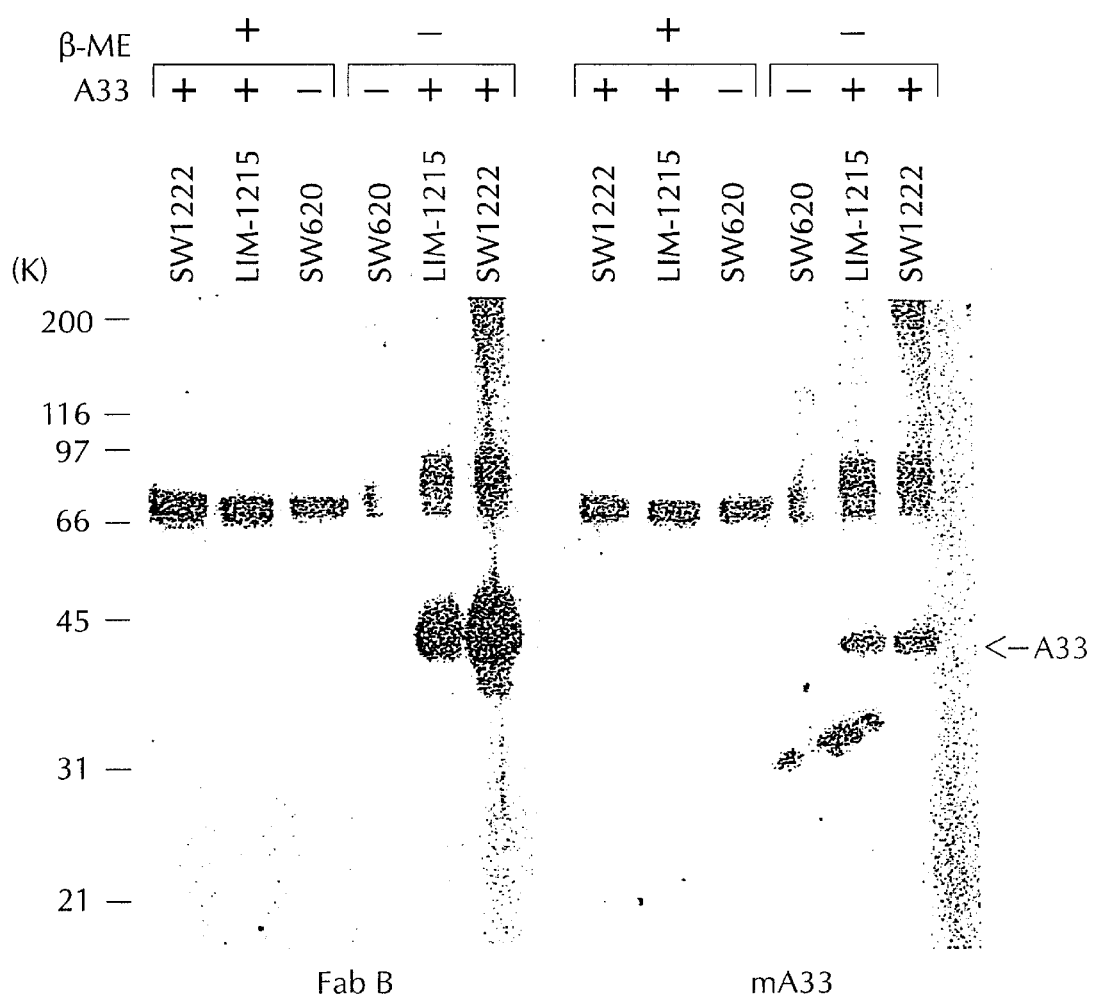
FIG. 2 depicts Western blot reactivity of human Fab B with Triton X-100 extracts of human A33 antigen expressing (LIM 1215, SW1222) and nonexpressing (SW620) human colon cancer cell lines. Specific binding was detected by alkaline-phosphatase-conjugated goat anti-human $F(ab^1)_2$ polyclonal antibodies and visualized using chemiluminescence. Numbers on the left indicate molecular masses of standard proteins in kilodaltons ("kDs").
Figure 3A:
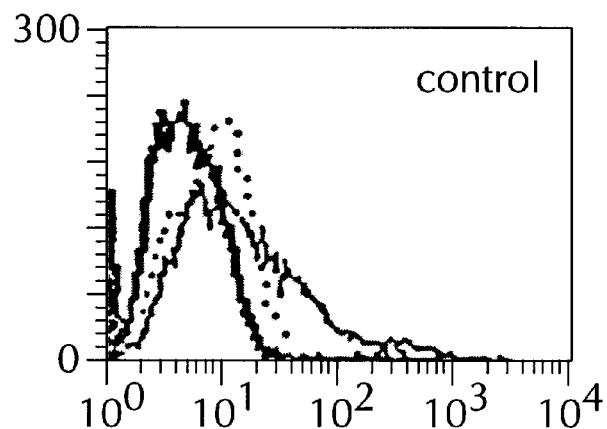
FIG. 3 depicts flow cytometry histograms demonstrating that the selected rabbit clones 1 and 2 as well as the selected human clones A–F bind specifically to native human A33 antigen expressed on the cell surface. For indirect immunofluorescence staining, cells were incubated with Fab (except for the control) followed by FITC-conjugated secondary antibodies. Human colon cancer cell lines LIM1216 (bold line) and SW1222 (fine line) are known to express human A33 antigen, whereas HT29 (dotted line) is known not to. They axis gives the number of events in linear scale, the x axis the fluorescence intensity in logarithmic scale.
Figure 3B:
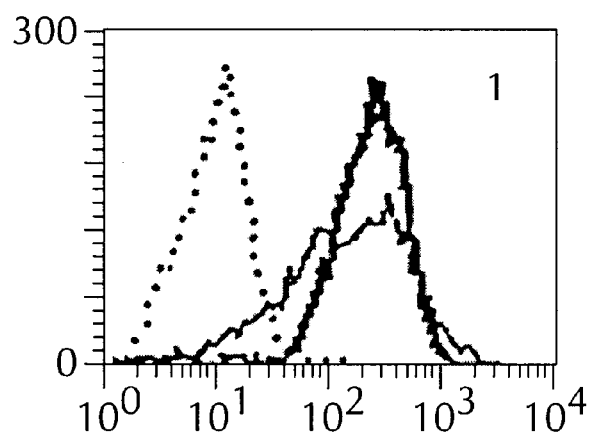
Figure 3C:
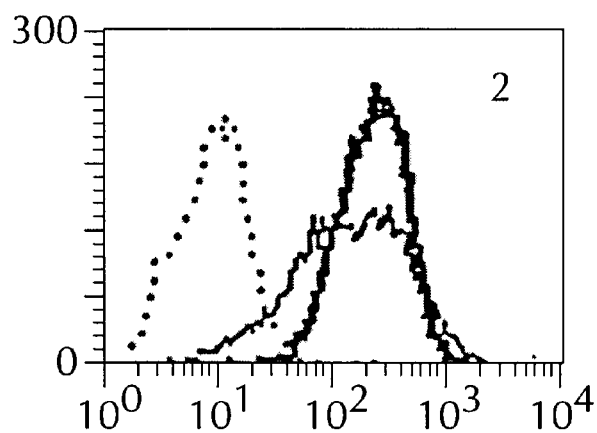
Figure 3D:
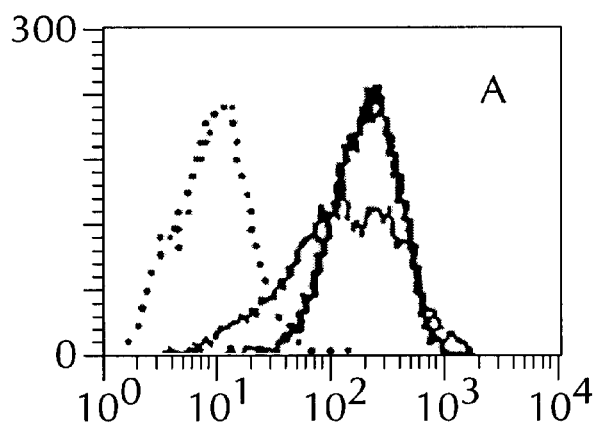
Figure 3E:
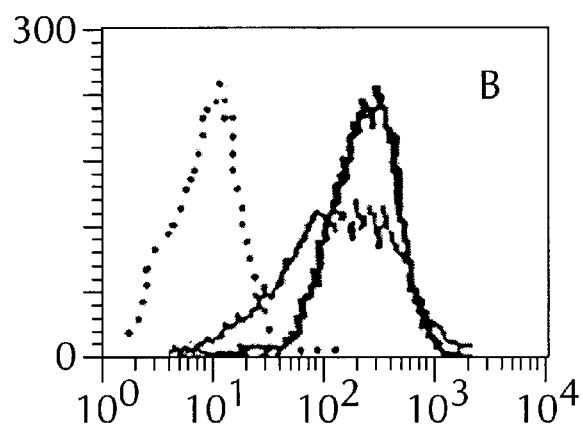
Figure 3F:
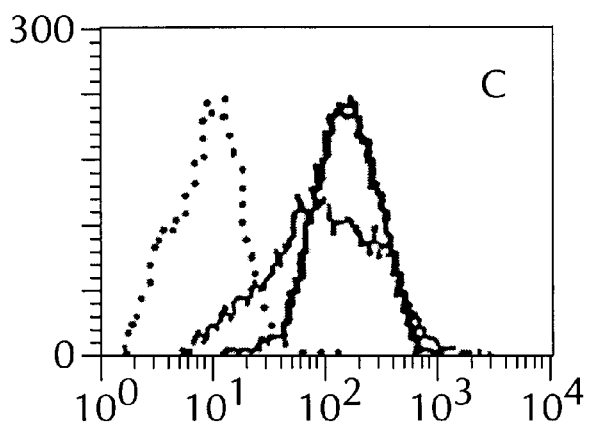
Figure 3G:
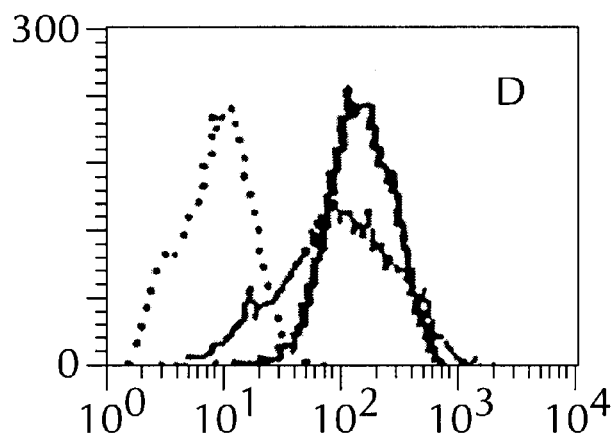
Figure 3H:
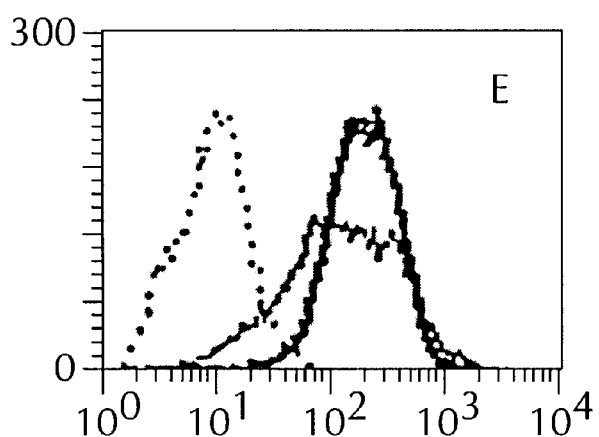
Figure 3I:
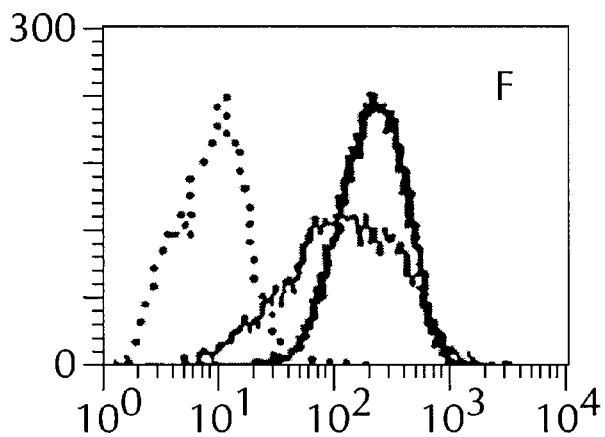

Insert: A DNA sequence foreign to the host, consisting of a structural gene and optionally additional DNA sequences.

Structural gene: A nucleic acid molecule coding for a polypeptide and being in operable linkage with a suitable promoter, termination sequence and optionally other regulatory DNA sequences.

Promoter: A recognition site on a DNA sequence or group of DNA sequences that provide an expression control element for a gene and to which RNA polymerase specifically binds and initiates RNA synthesis (transcription) of that sequence.

Inducible promoter: A promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

Multimeric protein: A globular protein containing more than one separate polypeptide or protein chain associated with each other to form a single protein. Both heterodimeric and homodimeric proteins are multimeric proteins.

Polypeptide and peptide: A linear series of amino acid residues connected one to the other by peptide bonds between the alpha-amino and carboxy groups of adjacent residues.

Protein: A linear series of greater than about 50 amino acid residues connected one to the other as in a polypeptide.

Fab fragment: A protein consisting of the portion of an immunoglobulin molecule containing the immunologically active portions of an immunoglobulin heavy chain and an immunoglobulin light chain covalently coupled together and capable of specifically combining with antigen. Fab fragments are typically prepared by proteolytic digestion of substantially intact immunoglobulin molecules with papain using methods that are well known in the art; however, a Fab fragment may also be prepared by expressing the desired portions of immunoglobulin heavy chain and immunoglobulin light chain in a host cell, using methods well known in the art.

$F_v$ fragment: A protein consisting of the immunologically active portions of an immunoglobulin heavy chain variable region and an immunoglobulin light chain variable region covalently coupled together and capable of specifically combining with antigen. $F_v$ fragments are typically prepared by expressing the desired portions of immunoglobulin heavy chain variable region and immunoglobulin light chain variable region in a host cell using methods well known in the art.

$V_L$CDR1, $V_L$CDR2, and $V_L$CDR3 denote immunoglobulin light chain complementarity determining region 1, 2 and 3 respectively.

$V_H$CDR1, $V_H$CDR2, and $V_H$CDR3 denote immunoglobulin heavy chain complementarity determining region 1, 2 and 3 respectively.

$V_L$FR1, $V_L$FR2, and $V_L$FR3 $V_L$FR4 denote immunoglobulin light chain framework region 1, 2, 3 and 4 respectively.

$V_H$FR1, $V_H$FR2, and $V_H$FR3 $V_H$FR4 denote immunoglobulin heavy chain framework region 1, 2, 3 and 4 respectively.

Immunoglobulin superfamily molecule: A molecule that has a domain size and amino acid residue sequence that is significantly similar to immunoglobulin or immunoglobulin related domains. The significance of similarity is determined statistically using a computer program such as the Align program described by Dayhoff et al., Meth Enzymol., 91:524–545 (1983) incorporated by reference. A typical Align score of less than 3 indicates that the molecule being tested is a member of the immunoglobulin gene superfamily. Exemplary of immunoglobulin superfamily molecules include the following members: immunoglobulin heavy chains (i.e., the heavy chain of IgM, IgD, IgG, IgA or IgE and light chains κ and λ), T cell receptors (α, β, γ, X, CD3), major histocompatibility antigens (Class I H-chain, $β_2$-microglobulin, Class II (α and β)), $β_2$-microglobulin associated antigens (TL H chain, Qa-2 H chain, CD1a H chain), T lymphocyte antigens (CD2, CD4, CD7, CD8 chain I, CD8 Chain IId, CD28 and CTLA4), haemopoietic/endothelium antigens (LFA-3, MRC OX-45), brain/lymphoid antigens (Thy-1, MRC OX-2), immunoglobulin receptors (Poly Ig R, Fc gamma 2b/gamma 1R, FcεRI(α)), neural molecules (Neural adhesion molecule, Myelin associated gp, P₀ myelin protein, Tumor antigen (carcinoembryonic antigen (CEA)), growth factor receptors (platelet-derived growth factor (PDGF) receptor, colony stimulating factor-1 (CSF1) receptor), non-cell surface molecules ($\alpha_1$ B-glycoprotein, basement membrane link protein) and A33 antigen (Heaths et al., Proc Natl Acad Sci 94:469–474 (1997)) (See e.g., Williams and Barclay, in Immunglobulin Genes, p 361, Academic Press, NY (1989); and Sequences of Proteins of Immunological Interest, 4th ed., U.S. Dept. of Health and Human Serving (1987)).

Epitope: A portion of a molecule that is specifically recognized by an immunoglobulin product. It is also referred to as the determinant or antigenic determinant.

Bispecific antibody (or heteroantibodies): A multivalent antibody containing binding sites specific for two different antigenic determinants. A bispecific antibody may be chemically synthesized as antibody heteroconjugates (AHCs) by covalently attaching two whole monoclonal antibodies ("whole AHCs") (B. Karpovsky, et al. (1984) J. Exp. Med. 160(6):1686–1701) or by attaching two monoclonal antibody Fab or Fab' fragments ("monovalent AHCs") (M. Brennan, et al., Science (1985) 229:(1708):81–83), where each antibody or antibody fragment has a different antigenic specificity. Alternatively, bispecific antibodies may be produced from a "hybrid hybridoma," a cell fusion of two monoclonal antibody-producing cells (C. L. Reading, in Hybridomas and Cellular Immortality, B. H. Tom et al., eds., 1984, (New York: Plenum Press), p. 235; U. D. Staerz et al., Proc. Natl. Acad. Sci. (1986) 83: 1453–1457; A. Lanzavecchia et al., Eur. J. Immunol. (1987)17:105–111; D. B. Ring et al., in Breast Epithelial Antigens: Molecular Biology to Clinical Applications, R. Cedani, ed., 1991, (New York: Plenum Press), pp. 91–104).

B. Methods of Producing a Humanized Antibody

One embodiment of the invention is directed to a method for producing a humanized antibody as a portion of a humanized antibody which binds to a specific antigen. The method comprises the steps of immnunizing a rabbit with an amount of a specific antigen which is specific to provoke an immune response, isolating RNA from antibody producing cells of the rabbit, converting the RNA to cDNA, and combining a portion of the cDNA which encodes for a portion of a rabbit antibody which binds to the antigen with a cDNA molecule which encodes a non binding portion of a human antibody, to form a hybrid molecule consisting of rabbit cDNA and human cDNA. Thereafter, the hybrid molecule is inserted into a host cell, and the host cell is cultured to express a protein product of the hybrid molecule. Finally, the hybrid protein is isolated.

The humanized antibody or a portion of the humanized antibody may consist of rabbit CDR and human constant regions. The humanized antibody may be a Fab fragment. Further, the antigen may be a molecule or portion of a molecule presented on a cell surface. For example, the antigen may be a molecule or portion of a molecule presented on a cell surface of a neoplastic (e.g., cancer) cell. The cancer cell may be a colon cancer cell. In one specific embodiment of the invention, the antigen may be an A33 antigen. The host cell used may be a prokaryotic cell such as an *E. coli* cell.

Another embodiment of the invention is directed to a humanized antibody made by any of the methods described above. The humanized antibody may comprise the amino acid sequence of SEQ ID NOS: 20, 21, 22, 39, 40, 41, 42, 43, 44, 45, 46, 47, 48, 49, 50, 51, 52, 53, 54, 55, 56, 57, 58, 59, 60, 61, 62, 63, 64, 65, 66 or 67.

C. Immunoglobulin Products Against A33 Antigen

One embodiment of the invention is directed to an immunoglobulin product that binds with specificity to an A33 antigen. An immunoglobulin product is a polypeptide, protein or multimeric protein containing at least the immunologically active portion of an immunoglobulin heavy chain or an immunologically active portion of an immunoglobulin light chain and is thus capable of specifically combining with an antigen. Exemplary immunoglobulin products are an immunoglobulin heavy chain, immunoglobulin light chain, immunoglobulin molecules, bispecific antibodies, substantially intact immunoglobulin molecules, any portion of an immunoglobulin that contains the paratope, including those portions known in the art as Fab fragments, Fab' fragment, F(ab')₂ fragment and Fv fragment. The structures of immunoglobulin products are well known to those skilled in the art and described in Basic and Clinical Immunology, by Stites, et al., 4th ed., Lange Medical Publications, Los Altos, Calif.

Another embodiment of the invention is directed to an immunoglobulin product such as an immunoglobulin molecule that binds with specificity to an A33 antigen. An immunoglobulin molecule is a multimeric protein containing the immunologically active portions of an immunoglobulin heavy chain and immunoglobulin light chain covalently coupled together and capable of specifically combining with antigen. It should be noted that the immunoglobulin molecule may be a bispecific antibody with affinity for A33 and a second non-A33 epitope.

Another embodiment of the invention is directed to a single-chain antigen-binding protein that binds with specificity to an A33 antigen. A single chain antigen binding protein is a polypeptide composed of an immunoglobulin light-chain variable region amino acid sequence ($V_L$) tethered to an immunoglobulin heavy-chain variable region amino acid sequence ($V_H$) by a peptide that links either (1) the carboxyl terminus of the $V_L$ sequence to the amino terminus of the $V_H$ sequence or (2) the carboxyl terminus of the $V_H$ sequence to the amino terminus of the $V_L$ sequence. A single-chain antigen-binding protein-coding gene, a recombinant gene coding for a single-chain antigen-binding protein, which encodes a single-chain antigen-binding protein that bind with specificity to an A33 antigen is also contemplated by this invention. The structure of single chain antigen binding proteins has been described by, e.g., Bird et al., Science, 242:423–426 (1988) and U.S. Pat. No. 4,704,692 by Ladner.

The immunoglobulins, or antibody molecules, are a large family of molecules that include several types of molecules, such as IgD, IgG, IgA, IgM and IgE. The antibody molecule typically includes two heavy (H) and two light (L) chains, each of which has a variable (V) and constant (C) region. Several different regions of an immunoglobulin molecule contain conserved sequences useful for isolating the immunoglobulin genes using the polymerase chain reaction. Extensive amino acid and nucleic acid sequence data displaying exemplary conserved sequences is compiled for immunoglobulin molecules by Kabat et al., in Sequences of Proteins of Immunological Interest, National Institute of Health, Bethesda, Md. (1987), incorporated by reference.

The V region of the H or L chain typically comprises four framework (FR) regions (FIG. 1) each containing relatively lower degrees of variability that includes lengths of conserved sequences.

One particularly useful immunoglobulin product is an immunoglobulin heavy chain. An immunoglobulin heavy chain consists of an immunoglobulin heavy chain variable region and an immunoglobulin heavy chain constant region. The immunoglobulin heavy chain variable region is a polypeptide containing an antigen binding site (and antibody combining site). The immunoglobulin heavy chain variable region is capable of specifically binding a particular epitope. Preferably, the $V_H$ will be from about 110 to about 125 amino acid residues long. The amino acid residue sequence will vary widely, depending on the particular epitope the $V_H$ is capable of binding.

One embodiment of the invention is directed to a method of reducing the effects of colon cancer in a subject. In the method, a pharmaceutically effective amount of an anti-cancer agent is conjugated to an immunoglobulin product that binds with specificity to A33 antigens. This anti-cancer agent-immunoglobulin product is conjugate is administered to a subject which has colon cancer to reduce the effects of the cancer. In particular, the immunoglobulin product comprises one or more CDRs having a sequence selected from the group consisting of LASEFLFNGVS (SEQ ID NO:68),
LASDFLFNGVS (SEQ ID NO:69),
GASNLES (SEQ ID NO:70),
GASDLET (SEQ ID NO:71),
LGGYSGSSGLT (SEQ ID NO:72),
LGGYSGSAGLT (SEQ ID NO:73),
HYGIS (SEQ ID NO:74),
NNGIS (SEQ ID NO:75),
YIYPNYGSVDYASSVNG (SEQ ID NO:76),
YIYPNYGSVDYASWVNG (SEQ ID NO:77),
YIYPDYGSTDYASWVNG (SEQ ID NO:78),
DRGYYSGSRGTRLDL (SEQ ID NO:79), and
DRGAYAGSRGTRLDL (SEQ ID NO:80).

The anti-cancer agent may be a drug selected from the group consisting of calicheamicin, BCNU, streptozoicin, vincristine and 5-fluorouracil. In addition, the anti-cancer agent may be a peptide that specifically inhibits DNA activity of said colon cancer. Other anti-cancer agents that may be used include a radioactive isotope such as $^{125}I$, $^{131}I$, $^{99}Tc$, $^{90}Y$ or $^{111}In$.

The immunoglobulin product of this invention may also comprise an immunologically active portion of an immunoglobulin light chain which has, for example, a $V_L$CDR1 region with a sequence of LASEFLFNGVS (SEQ ID NO:68) or LASDFLFNGVS (SEQ ID NO:69); a $V_L$CDR2 region with sequence GASNLES (SEQ ID NO:70) or GASDLET (SEQ ID NO:71); and a $V_L$CDR3 region with a sequence consisting of LGGYSGSSGLT (SEQ ID NO:72) or LGGYSGSAGLT (SEQ ID NO:73). In a preferred embodiment, $V_L$CDR1 has sequence LASEFLFNGVS (SEQ ID NO:68), $V_L$CDR2 has sequence GASNLES (SEQ ID NO:70) and $V_L$CDR3 has sequence LGGYSGSSGLT (SEQ ID NO:72).

The immunoglobulin product may contain an immunoactive portion of an immunoglobulin light chain. This light chain may contain a sequence in the $V_L$FR1 region which corresponds to one of the following sequences:

ELQMTQSPSSLSASVGDRVTITC (SEQ ID NO:81),
EFDMTQTPPSLSASVGETVRIRC (SEQ ID NO:82),
ELVMTQTPPSLSASVGETVRIRC (SEQ ID NO:83), or
ELVLTQTPPSLSPSVGETVRIRC (SEQ ID NO:84);

or a $V_L$FR2 region which corresponds to one of the following sequences:

WYQQKPGKAPKLLIY (SEQ ID NO:85),
WYQQKPGKAPKLLIY (SEQ ID NO:86)
WYQQKPGKVPKFLIY (SEQ ID NO:87),
WYQQKPGKAPKFLIY (SEQ ID NO:88),
WYQQKPGKVPKLLIY (SEQ ID NO:89),
WYQQKPGKPPKFLIS (SEQ ID NO:90), or
WYQQKPEKPPTLLIS.(SEQ ID NO:91);

or a $V_L$FR3 region which corresponds to one of the following sequences:

GVPSRFSGSGSGTDFTLTISSLQPEDVATYYC (SEQ ID NO:92),
GVPSRFSGSGSGTDYTLTISSLQPEDVATYYC (SEQ ID NO:93),
GVPSRFSGSGSGTDFTLTISSLQPEDVATYYC (SEQ ID NO:94),
GVPPRFSGSGSGTDYTLTIGGVQAEDVATYYC (SEQ ID NO:95), or
GVPPRFSGSGSGTDYTLTIGGVQAEDAATYYC (SEQ ID NO:96);

or a $V_L$FR4 region which corresponds to one of the following sequences:

FGGGTKVEIK (SEQ ID NO:97) or
FGAGTNVEIK.(SEQ ID NO:98).

In another embodiment, the immunoglobulin product may also comprise an immunologically active portion of an immunoglobulin heavy chain which has, for example, a $V_H$CDR1 having a sequence of HYGIS (SEQ ID NO:74) or NNGIS (SEQ ID NO:75); a $V_H$CDR2 sequence of YIYPNYGSVDYASSVNG (SEQ ID NO:76), YIYPNYGSVDYASWVNG (SEQ ID NO:77), or YIYPDYGSTDYASWVNG (SEQ ID NO:78); and a $V_H$CDR3 sequence of DRGYYSGSRGTRLDL (SEQ ID NO:79) or DRGAYAGSRGTRLDL (SEQ ID NO:80). In a preferred embodiment, $V_H$CDR1 has a sequence of HYGIS (SEQ ID NO:74), $V_H$CDR2 has a sequence of YIYPNYGSVDYASSVNG (SEQ ID NO:76); and $V_H$CDR3 has a sequence of DRGYYSGSRGTRLDL (SEQ ID NO:79).

The immunoglobulin product may contain an immunoactive portion of an immunoglobulin heavy chain. This heavy chain may contain a sequence in the $V_H$FR1 region which corresponds to one of the following sequences:

EVQVMESGGGLVKPGGSLRLSCAASGFTFS (SEQ ID NO:99),
EVQVMESGGGLVKPGGSLRLSCAASGIDFS (SEQ ID NO:100),
EVQVMESGGGLVKPGGSLRLSCAASGIGFS (SEQ ID NO:101),
QQQVMESGGGLVTLGGSLTLTCKASGIDFS (SEQ ID NO:102),
QEQLMESGGGLVTLGGSLKLSCKASGIDFS (SEQ ID NO:103), or
QEQVMESGGGLVTLGGSLKLSCKASGIDFS (SEQ ID NO:104);

or a $V_H$FR2 region which corresponds to one of the following sequences:

WVRQAPGKGLEWIL (SEQ ID NO:105),
WVRQAPGKGLEWIA (SEQ ID NO:106), or
WVRQAPGKGLEWVS.(SEQ ID NO:107);

or a $V_H$FR3 region which corresponds to one of the following sequences:

RFTISRDNAKNSLYLQMNSLRAEDTAVYYCAR (SEQ ID NO:108),
RFTISFDNAQNSLYLQMNSLRAEDTAVYYCAR (SEQ ID NO:109),
RFTISLDNAQNSLYLQMNSLRAEDTAVYFCAR (SEQ ID NO:110),

RFTISLDNAQNSLYLQMNSLRAEDTAVYYCAR (SEQ ID NO:111),
RFTISFDNAQNSVYLQMNSLRAEDTAVYYCAR (SEQ ID NO:112),
RFTISRDNAKNSLYLQMNSLRAEDTAVYYCAR (SEQ ID NO:113),
RFTISRDNAKNSLYLQMNSLRAEDTAVYFCAR (SEQ ID NO:114),
RFTISRDNAKNSVYLQMNSLRAEDTAVYYCAR (SEQ ID NO:115),
RFTISRDNAKNSVYLQMNSLRAEDTAVYFCAR (SEQ ID NO:116),
RFTISLDNAQNSLYLQMNSLRAEDTAVYYCAR (SEQ ID NO:117),
RFTISLDNAQNSLYLQMNSLRAEDTAVYFCAR (SEQ ID NO:118),
RFTISLDNAQNSVYLQMNSLRAEDTAVYYCAR (SEQ ID NO:119),
RFTISLDNAQNSVYLQMNSLRAEDTAVYFCAR (SEQ ID NO:120),
RFTISSDNAQNSLYLQMNSLRAEDTAVYYCAR (SEQ ID NO:121),
RFTISSDNAQNSLYLQMNSLRAEDTAVYFCAR (SEQ ID NO:122),
RFTISSDNAQNSVYLQMNSLRAEDTAVYYCAR (SEQ ID NO:123), or
RFTISSDNAQNSVYLQMNSLRAEDTAVYFCAR (SEQ ID NO:124);
or a $V_H$FR4 region which corresponds to one of the following sequences:
WGQGTLVTISS (SEQ ID NO:125), or
WGQGTLVTVSS.(SEQ ID NO:126)

In another embodiment, the immunoglobulin product may comprise an immunologically active portion of an immunoglobulin light chain which has (A) a $V_L$ CDR1 region with a sequence of LASEFLFNGVS (SEQ ID NO:68) or LASDFLFNGVS (SEQ ID NO:69); a $V_L$ CDR2 region with a sequence of GASNLES (SEQ ID NO:70) or GASDLET (SEQ ID NO:71); and a $V_L$ CDR3 region with a sequence of LGGYSGSSGLT (SEQ ID NO:72) or LGGYSGSAGLT (SEQ ID NO:73); and (B) a $V_H$CDR1 having a sequence of HYGIS (SEQ ID NO:74) or NNGIS (SEQ ID NO:75); a $V_H$CDR2 sequence of YIYPNYGSVDYASSVNG (SEQ ID NO:76), YIYPNYGSVDYASWVNG (SEQ ID NO:77), or YIYPDYGSTDYASWVNG (SEQ ID NO:78); and a $V_H$CDR3 sequence of DRGYYSGSRGTRLDL (SEQ ID NO:79) or DRGAYAGSRGTRLDL (SEQ ID NO:80).

In a preferred embodiment, the immunoglobulin product of the invention binds to A33 antigen with an affinity which is stronger than 500 pM. More preferably, the immunoglobulin product of the invention binds to A33 antigen with an affinity which is stronger than 100 pM.

Another embodiment of the invention is directed to a substantially pure immunoglobulin product that binds with specificity to A33 antigen. The immunoglobulin product may comprise one or more sequences of amino acids having the sequence of
LASEFLFNGVS (SEQ ID NO:68),
LASDFLFNGVS (SEQ ID NO:69),
GASNLES (SEQ ID NO:70),
GASDLET (SEQ ID NO:71),
LGGYSGSSGLT (SEQ ID NO:72),
LGGYSGSAGLT (SEQ ID NO:73),
HYGIS (SEQ ID NO:74),
NNGIS (SEQ ID NO:75),
YIYPNYGSVDYASSVNG (SEQ ID NO:76),
YIYPNYGSVDYASWVNG (SEQ ID NO:77),
YIYPDYGSTDYASWVNG (SEQ ID NO:78),
DRGYYSGSRGTRLDL (SEQ ID NO:79), or
DRGAYAGSRGTRLDL (SEQ ID NO:80).

In one embodiment, the substantially pure immunoglobulin product which binds the A33 antigen contains an immunologically active portion of an immunoglobulin light chain that in turn contains one or more light chain CDRs. For example, the immunoglobulin light chain, $V_L$CDR1 may have sequence LASEFLFNGVS (SEQ ID NO:68) or LASDFLFNGVS (SEQ ID NO:69); $V_L$CDR2 may have sequence GASNLES (SEQ ID NO:70) or GASDLET (SEQ ID NO:71); and $V_L$CDR3 may have a sequence LGGYSGSSGLT (SEQ ID NO:72) or LGGYSGSAGLT (SEQ ID NO: 73). In a preferred embodiment, $V_L$CDR1 is LASEFLFNGVS (SEQ ID NO:68), $V_L$CDR2 is GASNLES (SEQ ID NO:70) and $V_L$CDR3 is LGGYSGSSGLT (SEQ ID NO:72).

In another embodiment, the substantially pure immunoglobulin product which binds the A33 antigen contains an immunologically active portion of an immunoglobulin heavy chain that in turn contains one or more CDRs of a heavy chain. For example, in the immunoglobulin heavy chain, $V_H$CDR1 may have sequence HYGIS (SEQ ID NO:74) or NNGIS (SEQ ID NO:75); $V_H$CDR2 may have sequence YIYPNYGSVDYASSVNG (SEQ ID NO:76), YIYPNYGSVDYASWVNG (SEQ ID NO:77), or YIYPDYGSTDYASWVNG (SEQ ID NO:78); and $V_H$CDR3 may have sequence DRGYYSGSRGTRLDL (SEQ ID NO:79) or DRGAYAGSRGTRLDL (SEQ ID NO:80). In a preferred embodiment $V_H$CDR1 is HYGIS (SEQ ID NO:74), $V_H$CDR2 is YIYPNYGSVDYASSVNG (SEQ ID NO:76), $V_H$CDR3 is DRGYYSGSRGTRLDL (SEQ ID NO:79).

In another preferred embodiment, the immunoglobulin product comprises at least two polypeptide sequences selected from the following: rabbit VL1 and rabbit VH1; rabbit VL2 and rabbit VH2; rabbit VL3 and rabbit VH3; human VLA and human VHA, human VLB and human VHB, human VLC and human VHC, human VLD and human VHD, human VLE and human VHE, or human VLF and human VHF.

In another embodiment, the substantially pure immunoglobulin product may comprise an immunologically active portion of an immunoglobulin heavy chain and an immunologically active portion of an immunoglobulin light chain. For example, in the active portion immunoglobulin light chain, $V_L$CDR1 may have sequence LASEFLFNGVS (SEQ ID NO:68) or LASDFLFNGVS (SEQ ID NO:69); $V_L$CDR2 may have sequence GASNLES (SEQ ID NO:70) or GASDLET (SEQ ID NO:71); and $V_L$CDR3 may have sequence LGGYSGSSGLT (SEQ ID NO:72) or LGGYSGSAGLT (SEQ ID NO:73). Further, in the active portion immunoglobulin heavy chain, $V_H$CDR1 may have sequence HYGIS (SEQ ID NO:74) or NNGIS (SEQ ID NO:75); $V_H$CDR2 may have sequence YIYPNYGSVDYASSVNG (SEQ ID NO:76), YIYPNYGSVDYASWVNG (SEQ ID NO:77), or YIYPDYGSTDYASWVNG (SEQ ID NO:78); and $V_H$CDR3 may have sequence DRGYYSGSRGTRLDL (SEQ ID NO:79) or DRGAYAGSRGTRLDL (SEQ ID NO:80).

An immunoglobulin product of the invention may be an antibody, a Fv fragment, a Fab fragment, a Fab$_2$ fragment, or a single chain antibody or a combination or multimer thereof. A multimer may be any linked combination of immunoglobulin products. For example, a multimer may contain more than 2, preferably more than 4, or even more than 6 antibodies, antibody fragments, or single chain antibodies linked together. Linkage may be by covalent bonds. Methods of linking antibodies and polypeptides, and proteins are known. Further, the linkage may be ionic. For example, one antibody linked to avidin may be linked by ionic bond to another antibody linked to biotin. The linked immunoglobulin products need not have the same affinity. For example, one linked immunoglobulin product may have a high affinity for A33 antigen, another linked immunoglobulin product may have a low affinity for A33 antigen, and a third linked immunoglobulin product may have an affinity to a toxic or therapeutic chemical such as ricin.

The immunoglobulin product may be an antibody molecule such as a IgM, IgD, IgG, IgA or IgE or a fragment of these molecules. The immunoglobulin product may bind A33 antigen with an affinity that is stronger than 1 pM, preferably stronger than 10 pM, more preferably stronger than 100 pM, even more preferably stronger than 300 pM such as, for example, stronger than 500 pM.

The immunoglobulin product may be an anti A33 antigen immunoglobulin product that is derived from a rabbit. A rabbit derived anti A33 antigen immunoglobulin product may be made, for example, by injecting a rabbit with A33 antigen. Another method for producing rabbit anti A33 antigen immunoglobulin product is shown in the Example section.

Another embodiment of the invention is directed to a CDR peptide and proteins that contain one or more CDR peptides with a sequence of LASEFLFNGVS (SEQ ID NO:68), LASDFLFNGVS (SEQ ID NO:69), GASNLES (SEQ ID NO:70), GASDLET (SEQ ID NO:71), LGGYSGSSGLT (SEQ ID NO:72), LGGYSGSAGLT (SEQ ID NO:73), HYGIS (SEQ ID NO:74), NNGIS (SEQ ID NO:75), YIYPNYGSVDYASSVNG (SEQ ID NO:76), YIYPNYGSVDYASWVNG (SEQ ID NO:77), YIYPDYG-STDYASWVNG (SEQ ID NO:78), DRGYYSG-SRGTRLDL (SEQ ID NO:79), or DRGAYAGSRGTRLDL (SEQ ID NO:80).

The immunoglobulin product of the invention may be a member of an immunoglobulin gene superfamily such as a immunoglobulin heavy chain, a T cell receptor, a major histocompatibility antigen, a $\beta_2$-microglobulin associated antigen, a T lymphocyte antigens, a haemopoietic/endothelium antigens, a brain/lymphoid antigen, an immunoglobulin receptor, a neural molecule, a tumor antigen and the like.

In addition, the immunoglobulin product of the invention may contain immunologically active portion of an immunoglobulin light chain. The active portion may be $V_L$FR1 with a sequence of ELQMTQSPSSLSASVGDRVTITC (SEQ ID NO:81), EFDMTQTPPSLSASVGETVRIRC (SEQ ID NO:82), ELVMTQTPPSLSASVGETVRIRC (SEQ ID NO:83), or ELVLTQTPPSLSPSVGETVRIRC (SEQ ID NO:84). Also, the active portion may be $V_L$FR2 having sequence WYQQKPGKAPKLLIY (SEQ ID NO:85), WYQQKPGKAPKLLIY (SEQ ID NO:86), WYQQKPGKVPKFLIY (SEQ ID NO:87), WYQQK-PGKAPKFLIY (SEQ ID NO:88), WYQQKPGKVPKLLIY (SEQ ID NO:89), WYQQKPGKPPKFLIS (SEQ ID NO:90), or WYQQKPEKPPTLLIS (SEQ ID NO:91). The active portion may be $V_L$FR3 with a sequence GVPSRF-SGSGSGTDFTLTISSLQPEDVATYYC (SEQ ID NO:92), GVPSRFSGSGSGTDYTLTISSLQPEDVATYYC (SEQ ID NO:93), GVPSRFSGSGSGTDFTLTISSLQPEDVATYYC (SEQ ID NO:94), GVPPRFSGSGSGTDYTLTIG-GVQAEDVATYYC (SEQ ID NO:95), or GVPPRFSGSGS-GTDYTLTIGGVQAEDAATYYC (SEQ ID NO:96). The active portion may also be $V_L$FR4 with sequence FGGGT-KVEIK (SEQ ID NO:97) or FGAGTNVEIK (SEQ ID NO:98).

The immunoglobulin product of the invention may contain immunologically active portion of an immunoglobulin heavy chain. The active portion may be $V_H$FR1 with a sequence of EVQVMESGGGLVKPGGSLRLSCAASG-FTFS (SEQ ID NO:99), EVQVMESGGGLVKPGGSL-RLSCAASGIDFS (SEQ ID NO:100), EVQVMESGGGLVKPGGSLRLSCAASGIGFS (SEQ ID NO:101), QQQVMESGGGLVTLGGSLTLTCKASGIDFS (SEQ ID NO:102), QEQLMESGGGLVTLGGSLKLSCK-ASGIDFS (SEQ ID NO:103), or QEQVMESGGGLVTLGGSLKLSCKASGIDFS (SEQ ID NO:104). The active portion may also be $V_H$FR2 with sequence WVRQAPGKGLEWIL (SEQ ID NO:105), WVRQAPGKGLEWIA (SEQ ID NO:106) or WVRQAPGKGLEWVS (SEQ ID NO:107). The active portion may also be $V_H$FR3 with sequence RFTISRD-NAKNSLYLQMNSLRAEDTAVYYCAR (SEQ ID NO:108), RFTISFDNAQNSLYLQMNSLRAED-TAVYYCAR (SEQ ID NO:109), RFTISLD-NAQNSLYLQMNSLRAEDTAVYFCAR (SEQ ID NO:110), RFTISLDNAQNSLYLQMNSLRAED-TAVYYCAR (SEQ ID NO:111), RFTISFDNAQNS-VYLQMNSLRAEDTAVYYCAR (SEQ ID NO:112), RFT-ISRDNAKNSLYLQMNSLRAEDTAVYYCAR (SEQ ID NO:113), RFTISRDNAKNSLYLQMNSLRAEDTAVY-FCAR (SEQ ID NO:114), RFTISRDNAKNSVYLQMNSL-RAEDTAVYYCAR (SEQ ID NO:115), RFTISRDNAKNS-VYLQMNSLRAEDTAVYFCAR (SEQ ID NO:116), RFTISLDNAQNSLYLQMNSLRAEDTAVYYCAR (SEQ ID NO:117), RFTISLDNAQNSLYLQMNSLRAEDTAVY-FCAR (SEQ ID NO:118), RFTISLDNAQNSVYLQMNSL-RAEDTAVYYCAR (SEQ ID NO:119), RFTISLDNAQNS-VYLQMNSLRAEDTAVYFCAR (SEQ ID NO:120), RFTISSDNAQNSLYLQMNSLRAEDTAVYYCAR (SEQ ID NO:121), RFTISSDNAQNSLYLQMNSLRAEDTAVY-FCAR (SEQ ID NO:122), RFTISSDNAQNSVYLQMNSL-RAEDTAVYYCAR (SEQ ID NO:123), or RFTISSD-NAQNSVYLQMNSLRAEDTAVYFCAR (SEQ ID NO:124). The active portion may also be $V_H$FR4 with sequence WGQGTLVTISS (SEQ ID NO:125) or WGQGTLVTVSS (SEQ ID NO:126).

In an embodiment of the invention, the substantially pure immunoglobulin product may be a humanized immunoglobulin.

Another embodiment is directed to a purified nucleic acid molecule encoding the substantially pure immunoglobulin product of the invention. A nucleic acid molecule encoding an immunoglobulin product of the invention may be made using conventional techniques. For example, oligonucleotides may be synthesized and ligated together to form a functional open reading frame that encodes an immunoglobulin product of the invention. The nucleic acid molecule, once synthesized, may be cloned into a nucleic acid vector. A nucleic acid vector such as a plasmid, cosmid, phagemid, yeast plasmid, phage vectors, TI plasmid and the like are known in the art. The vector may be an expression vector. Expression vectors and expression systems are available commercially.

Another embodiment of the invention is directed to a cell comprising a nucleic acid of the invention. A cell may be made by transfection. Methods of transfection are known and kits for transfection of prokaryotic and eukaryotic cells may be purchased from commercial sources.

Another embodiment of the invention is directed to a method for detecting or diagnosing a disorder comprising the steps of contacting a tissue sample from a subject to the substantially pure immunoglobulin product of the invention under condition that permits the formation of a complex between said immunoglobulin product and an A33 antigen, and determining the formation of said complex.

Another embodiment of the invention is directed to a method of treating a patient with a neoplastic disorder comprising administering an immunoglobulin product of invention or a nucleic acid of the invention to said patient. Methods for immunotherapy for cancer are known. See for example Old, L. J. Immunotherapy for Cancer, Scientific American, September 1996, U.S. Pat. Nos. 5,851,526 and 5,712,369; all incorporated herein by reference.

Another embodiment is directed to a therapeutic composition comprising an immunoglobulin product of the invention. The immunoglobulin products of the invention may be provided in the form of a composition comprising the immunoglobulin and a pharmaceutically acceptable carrier or diluent. The therapeutic composition may be used for the treatment of disorders in a mammal such as a human. The invention also provides a method for treating a mammal comprising administering a therapeutically effective amount of the immunoglobulin products of the invention to the mammal, wherein the mammal has a disorder, such as cancer, requiring treatment with the antibody.

In its use as a therapeutic agent, the immunoglobulin product of the invention may be linked to an agent. Linkage may be by covalent bonds or by antibody-epitope bond. For example, an immunoglobulin product may be crosslinked to a second antibody wherein the second antibody may have an affinity for the agent. The agent may be a cytotoxic agent. The term "cytotoxic agent" as used herein refers to a substance that inhibits or prevents the function of cells and/or causes destruction of cells. The term is intended to include radioactive isotopes (e.g., $^{125}$I, $^{131}$I, $^{99}$Tc, $^{90}$Y, $^{111}$In), chemotherapeutic agents, and toxins such as enzymatically active toxins of bacterial, fungal, plant or animal origin, or fragments thereof. The agent may be a chemotherapeutic agent. A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards. The agent may be a cytokine. The term "cytokine" is a generic term for proteins released by one cell population which act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon-$\alpha$, -$\beta$, and -$\gamma$, colony stimulating factors (CSFs); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL9, IL-11, IL-12; a tumor necrosis factor; and other polypeptide factors including LIF and kit ligand (KL). As used herein, the term cytokine includes proteins from natural sources or from recombinant cell culture and biologically active equivalents of the native sequence cytokines.

For diagnosis, the immunoglobulin product of the invention may be attached to a label. The word "label" when used herein refers to a detectable compound or composition which is conjugated directly or indirectly to the antibody. The label may be detectable by itself (e.g. radioisotope labels or fluorescent labels) or, in the case of an enzymatic label, may catalyze chemical alteration of a substrate compound or composition which is detectable.

The invention also contemplated the generation of mutants of the disclosed CDRs by mutating one or more amino acids in the sequence of one or more of the CDRs. It is known that a single amino acid substitution appropriately positioned in a CDR can be sufficient to raise the affinity. Researchers have used site directed mutagenesis to increase affinity of some immunoglobulin products by about 10 folds. This method of increasing or decreasing affinity of antibodies by mutating CDRs is common knowledge (see, e.g., Chapter 23, Paul, W. E., Fundamental Immunology, Raven Press, NY, N.Y. 1993). Thus, the substitution, deletion, or addition of amino acids to the CDRs of the invention to increase or decrease binding affinity or specificity is also within the contemplation of this invention.

EXAMPLE 1

Generation of Antibodies to Human A33 Antigen

In order to generate monoclonal antibodies to human A33 antigen, New Zealand white rabbits were immunized, over a 4–5 month period, with human colon carcinoma cell line LIM 1215, which is known to express large amounts of A33 antigen. It should be noted that LIM 1215 was chosen because it expresses A33 antigen. Any other cell line which expresses A33 antigen may be substituted for LIM 1215. Subject animals received three subcutaneous injections of $10^6$ LIM 1215 cells followed by three subcutaneous injections of 1 $\mu$g of extracellular domain of human A33 that had been purified from LIM 1215 cells. The A33 was administered in the form of a 1 ml emulsion of RIBI adjuvant in phosphate buffered saline.

This approach was taken in order to target hormonal immune responses to native epitopes of protein accessible on cell surfaces, which is key to developing therapeutically useful antibodies.

Antisera from the subject animals were tested following the three injections of LIM 1215 cells, and then the three injections of antigen. Testing was carried out by combining the antisera with recombinant human A33 and alkaline phosphatase conjugated, goat anti-rabbit Fc polyclonal antibodies.

The result indicated that there was a weak immune response following the injections with cells, and a strong immune response was observed following the three injections with antigen.

EXAMPLE 2
Amplification of Variable Region Sequences and Generation of Chimeric Antibodies Five days after the last of the six immunizations referred to supra, spleen and bone marrow cells from one leg were harvested from each animal. Total RNA was extracted from the cells, using standard methodologies. First strand cDNA was then synthesized from the RNA, using standard techniques. The cDNA was then amplified via PCR (35 cycles). Various primers were used, i.e.:

$V_\kappa$ 5' sense primers:
1. 5'-gggcccaggcggccgagctcgtgmtgacccagactcca-3' (SEQ ID NO:1)
2. 5'-gggcccaggcggccgagctcgatmtgacccagactcca-3' (SEQ ID NO:2)
3. 5'-gggcccaggcggccgagctcgtgatgacccagactgaa-3' (SEQ ID NO:3)

$V_k$ 3' antisense primers:
1. 5'-acagatggtgcagccacagttaggatctccagctcggtccc-3' (SEQ ID NO:4)
2. 5'-gacagatggtgcagccacagttttgatttccacattggtgcc-3' (SEQ ID NO:5)
3. 5'-gacagatggtgcagccacagttttgacsaccacctcggtccc-3' (SEQ ID NO:6)

$V_\lambda$ 5' sense primer:
5'-gggcccaggcggccgagctcgtgctgactcagtcgccctc-3' (SEQ ID NO:7)

$V_\lambda$ 3' antisense primer:
5'-cgaggggggcagccttgggctggcctgtgacggtcagctgggtccc-3' (SEQ ID NO:8)

To carry out the PCR, all nine possible combinations for amplification of $V_\kappa$ were used, as well as the single combination provided for $V_\lambda$. In addition, the four possible combinations provided by SEQ ID NOS: 9–13, i.e., V 5' sense primers:
1. 5'-gctgcccaaccagccatggcccagtcggtggaggagtccrgg-3' (SEQ ID NO:9)
2. 5'-gctgcccaaccagccatggcccagtcggtgaaggagtccgag-3' (SEQ ID NO:10)
3. 5'-gctgcccaaccagccatggcccagtcgytggaggagtccggg-3' (SEQ ID NO:11)
4. 5'-gctgcccaaccagccatggcccagsagcagctgrtggagtccgg-3' (SEQ ID NO:12)

V 3' antisense primer:
5'-cgatgggcccttggtggaggctgargagayggtgaccagggtgcc-3' (SEQ ID NO:13)

were used to amplify V. It should be noted that the antisense primers (SEQ ID NOS: 4–6,8 and 13) represent hybrids of rabbit and human sequences, and were designed to permit fusion of rabbit, variable domains to human constant domains (i.e., fusion of rabbit $V_\lambda$ or V to human CK and C 1). These human constant regions had been amplified from an expression vector containing a human Fab directed to tetanus toxoid. See, e.g., Rader, et al., Curr. Opin. Biotechnol 8(4):503–508 (1997). The procedure permitted assembly and fusion of chimeric rabbit/human light chain and Fd fragment coding sequences and two sequential overlap extension PCR steps. In the first step, the rabbi $V_\lambda$ and human CK fragments were fused using:

gaggaggagg aggaggaggc ggggcccagg cggccgagct c (SEQ ID NO:14), and gccatggctg gttgggcagc (SEQ ID NO:15), and rabbit V and human C 1 were fused using:

gctgcccaac cagccatggc c (SEQ ID NO:16) and gaggaggagg aggaggagag aagcgtagtc cggaacgtc (SEQ ID NO:17).

Then, assembled chimeric light chain and Fd fragment coding sequences were fused using SEQ ID NO: 14 and SEQ ID NO: 17. Only light chain and Fd fragment coding sequences from the same animal were combined. Final constructs were cloned into a phagemid vector, in accordance with Rader, et al., supra, to yield $2 \times 10^7$ independent transformants. This methodology has several advantages over approaches using a uniform Fab format with original, constant domains from a given species. First, notwithstanding the fact that antigen binding is confined to variable domains, and should not be expected to be influenced by constant domain swapping, the human constant domains provide established and standardized modes for detecting and purification, as compared to Fabs derived from multiple species. In addition, Ulrich et al., Proc. Natl. Acad Sci USA 92(25):11907–11 (1995), have shown that this approach improves *E. Coli* expression levels of Fab. Also, Fab molecules with human constant domains are partially humanized, and can be readily channeled into strategies for complete humanization, as reported by, e.g., Rader, et al., Proc. Natl. Acad Sci USA 95(15): 8910–8915 (1998), incorporated by reference.

EXAMPLE 3
Screening the Chimera Antibody

The phage library prepared in example 2, supra, was then panned against recombinant human A33 antigen using 200 ng of protein in 25 µl of TBS for coating on 1 well of a 96 well plate, 0.05% (v/v) Tween 20 in TBS for washing, and 10 mg/ml of trypsin in TBS for elution. Trypsinization was carried out for 30 minutes at 37° C. The number of washing steps increased from 5 (first round) to 10 (second round), to 15 in the third and fourth rounds.

Output phage pool of each round was monitored, via phage ELISA, using horseradish peroxidase labelled sheep anti-M13 phage polyclonal antibodies. Increased signal above background from round to round was observed, and output numbers increased strongly after the third and fourth rounds, indicating successful selection.

Forty clones from final output were grown and induced with 1 mM IPTG. Supernatants from the clones were tested for binding to immobilized, recombinant human A33 via ELISA, using alkaline phosphatase—conjugated goat, anti-human F(ab')$_2$ polyclonal antibodies. All clones gave a strong signal, above background, and were subjected to DNA fingerprinting using standard methodologies. In brief, flanking primers:

AAGACAGCTA TCGCGAATTG CAC (SEQ ID NO:18) and

GCCCCCTTAT TAGCCTTTGC CATC (SEQ ID NO:19)

were used, and digested with 4 base pair cutter BstXI. Three different but highly similar fingerprints were obtained. One was found in 13 clones, the second in 26 clones, and the third, in one clone. FIG. 1 presents these. Also see SEQ ID NOS: 20–22.

Analysis indicated that the sequences corresponding to variable domains were rabbit, and that the three clones were highly related. Clones 1 and 2 (SEQ ID NOS: 20 and 21) had identical VK coding sequences, and 90% identity in the V sequence. SEQ ID NO: 22 had a VK coding sequence 90% identical to SEQ ID NOS: 20 and 21, and its V sequence was identical to that of SEQ ID NO:22. The hypervariable VDJ and VJ joint regions HCDR3 and LCDR3 were highly similar, suggesting that all the selected sequences originated from a single B cell clone that had undergone diversification by somatic mutation.

EXAMPLE 4

Characterization of the Expressed Fabs

Figure 5:
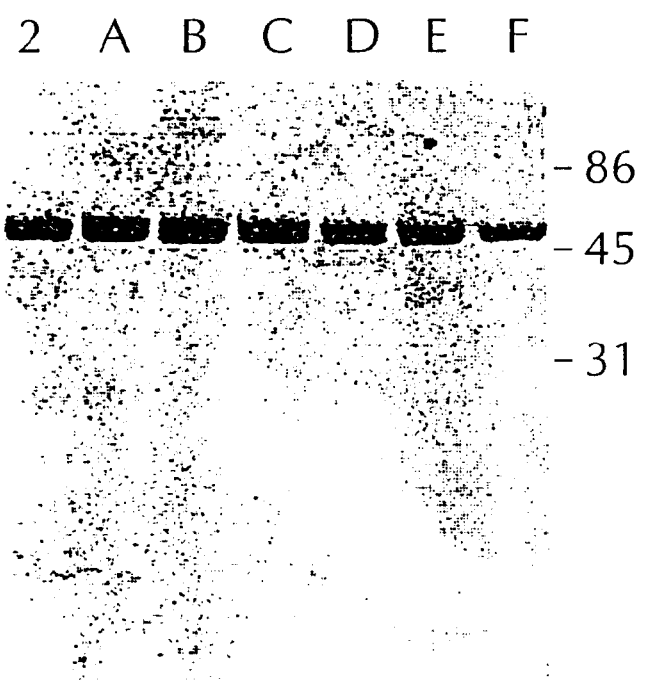
FIG. 5 depicts analysis of purified rabbit and humanized Fab by SDS-PAGE and Coomassie Blue staining. Fabs were purified from *E. coli* cultures by Protein G affinity chromatography. Numbers on the right indicate molecular masses of standard proteins in kD.

Soluble Fabs from rabbit VH1, VL1 and rabbit VH2 and VL2 were produced from E coli, in accordance with Rader, et al., supra. Fab molecules were purified from concentrated supernatants and from sonicated lysates of overnight cultures that had been induced with 1 mM IPTG, followed by affinity chromatography, using PBS as equilibration and washing buffer, and U.5M acetic acid for elution. The eluted fractions were neutralized immediately using 0.5 volumes 1M Tris-HCl, pH 9.0, followed by pooling. The materials were concentrated, and combined with PBS. Quality was analyzed via SDS-PAGE and Coomassie Blue staining, using standard methods (FIG. 5). They were then subjected to flow cytometry, using FACS scan. For each determination, $1 \times 10^4$ cells were analyzed. Indirect immunofluorescence staining was carried out using 2 mg/ml of Fab, in 1% w/v BSA, 25 mM Hepes, 0.05% (w/v) sodium azide in PBS. Dilutions (1:100) of FITC conjugated donkey anti-human F(ab$^1$)$_2$ polyclonal antibodies were used for detection. Incubation was carried out for 1 hour with primary antibodies and 30 minutes with the secondary antibodies, at room temperature. The results are plotted in FIG. 3.

The flow cytometry revealed that both Fabs specifically bound to cells that express natural A33 antigen. The binding strength was determined by surface plasmon resonance in accordance with Rader, et al., Proc. Natl. Acad. Sci USA 95(15): 8910–8915 (1998), incorporated by reference. Briefly, the determination of association ($k_{on}$) and dissociation ($k_{off}$) rate constants for binding of rabbit and humanized Fab to recombinant human A33 antigen was performed on a Biacore instrument (Biacore AB, Uppsala, Sweden). A CM5 sensor chip (Biacore AB) was activated for immobilization with Nhydroxysuccinimide and N-ethyl-N'-(3-dimethylaminopropyl)carbodiimide according to standard methods. Recombinant human A33 antigen was coupled at a low density to the surface by injection of 30 µl to 40 µl of a 1 ng/µl sample in 10 mM sodium acetate (pH 3.5). Approximately 500 resonance units were immobilized. Subsequently, the sensor chip was deactivated with 1 M ethanolamine hydrochloride (pH 8.5). Binding of Fab to immobilized A33 antigen was studied by injection of Fab at 5 different concentrations ranging from 75 nM to 200 nM. PBS was used as the running buffer. The sensor chip was regenerated with 20 mM HCl and remained active for at least 50 measurements. The $k_{on}$ and $k_{off}$ values were calculated using Biacore AB evaluation software. The equilibrium dissociation constant $K_d$ was calculated from $k_{off}/k_{on}$. Data obtained from different sensor chips revealed a high consistency and were further validated according to procedure as described in Rader et al., (Rader, C., Cheresh, D. A., and Barbas, C. F., III (1998) Proc. Natl. Acad. Sci. U.S.A. 95, 8910–8915, incorporated herein by reference).

Figure 6:
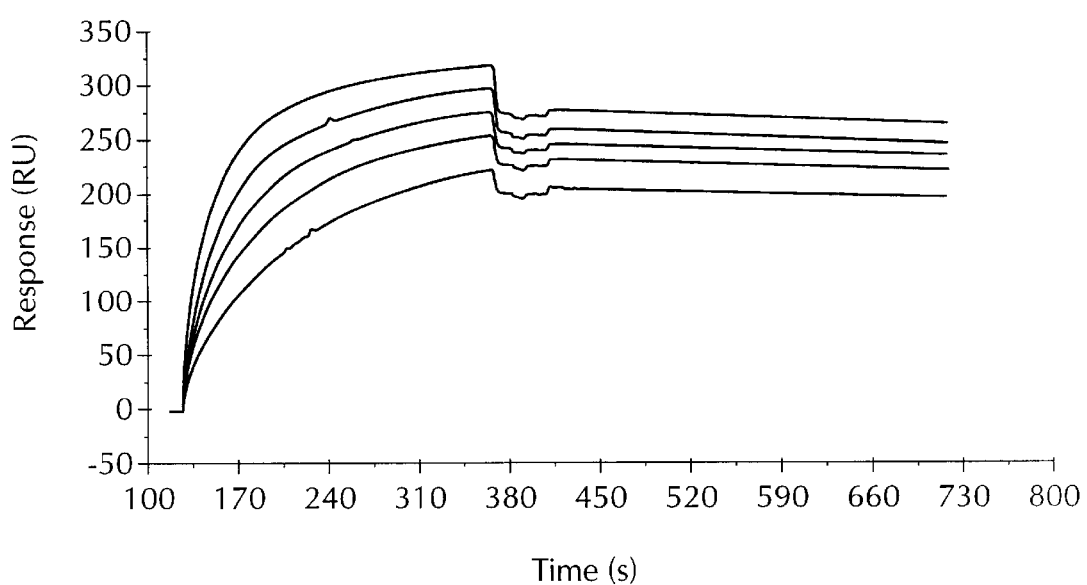
FIG. 6 depicts representative Biacore sensorgrams obtained for the binding of rabbit Fab 1 to immobilized human A33 antigen. For association, Fab were injected at 5 different concentrations (200 nM, 150 nM, 125 nM, 100 nM, 75 nM, top to bottom) between t=125 and t=370 seconds, using a flow rate of 5 µl/minute. For dissociation, the flow rate was increased to 50 µl/minute resonance units (RU).

The binding of the Fab was very strong, i.e., with affinity in the 1 nM range (FIG. 4). Kd values for SEQ ID NOS: 20 and 21 were 390 pM and 1.6 nM, respectively (FIG. 6, Table I). While SEQ ID NO: 20 showed higher association and slower dissociation rates, SEQ ID NO: 21 gave consistently higher yields. This, taken with the fact that the majority of clones contained SEQ ID NO: 21, suggests that the higher expression level competes well with the stronger affinity of SEQ ID NO: 20.

TABLE I

| Clone | $k_{on}/10^4$ (M$^{-1}$ s$^{-1}$) | $k_{off}/10^{-4}$ | $K_d$ |
|---|---|---|---|
| rabbit 1 | 30.7 +/− 0.9 | 1.2 +/− 0.1 | 0.39 |
| rabbit 2 | 17.4 +/− 1.0 | 2.8 +/− 0.2 | 1.6 |
| humanized A | 10.5 +/− 0.7 | 5.9 +/− 0.1 | 5.6 |
| humanized B | 35.2 +/− 1.5 | 6.1 +/− 0.1 | 1.7 |
| humanized C | 10.9 +/− 0.3 | 19.7 +/− 0.3 | 18.1 |
| humanized D | 6.5 +/− 0.3 | 19.0 +/− 0.6 | 29.2 |
| humanized E | 6.5 +/− 0.2 | 5.0 +/− 0.1 | 7.7 |
| humanized F | 19.2 +/− 1.2 | 6.8 +/− 0.2 | 3.5 |

Association ($k_{on}$) and dissociation ($k_{off}$) rate constant were determined using surface plasmon resonance.
Human antigen A33 was immobilized on the sensor chip.
The dissociation constant ($K_d$) was calculated from $k_{on}/k_{off}$.

EXAMPLE 5

Humanization of Selected Rabbit Variable Domains

These experiments describe the humanization of the selected, rabbit variable domains described supra. First the VBASE Directory of Human V Gene sequences (www.mrc-cpe.cam.ac.uk/imt-doc1) was screened, using amino acid sequence alignment, to identify human germ-line $V_\lambda$ and $V_\kappa$ sequences having the highest degree of homology with the rabbit sequences described herein. To elaborate, the rabbit sequences were first aligned with human V and J genes. Human V gene DP-77 (3–21), from the $V_H 3$ family, and human J gene $J_H 1$ showed highest homology. The Vκ sequence (rabbit) used gave a best match with human V gene DPK4(A20) from Vκ1 family, and human J gene Jκ4. These human sequences not only gave the best alignment with the rabbit sequences, but are found, frequently, in the human antibody repertoire. See deWildt, et al., J. Mol. Biol 285(3):895–901 (1999). Further, they are highly related to human V genes DP-47 (3–23), and DPK-9(02), the frameworks of which have both been used for mouse antibody hybridizations, and both of which give high yields when expressed in E.coli. See, e.g., Presta, et al., Canc. Res 57(20):4593–9 (1997). Indeed, pairs of $V_H 3$ family heavy chains and Vκ1 family light chains are the most frequent combination found in native human antibodies. This suggests that the combination is immuno silent.

The CDR sequence of SEQ ID NO: 2 was used because of high expression. The six variable domains described by Kabat, et al., supra, were grafted into human framework sequences. There was a potentially immunogenic tryptophan at position 62, in rabbit "HCDR2" (Kabat et al., supra), was converted to serine.

"Fine tuning" of frameworks was accomplished by diversifying 6 positions in human V framework, and 4 in human Vκ framework (Table II). The residues chosen were selected from key framework residues known to be involved in antigen binding. Analysis of these human sequences indicated that they are diversified at positions that are potentially involved in antigen binding. These sequences were used as framework for grafting of the six rabbit CDRs described by Kabat, et al., *Sequences of Proteins of Immunological Interest)* (5$^{th}$ edition, US Dept. of Health and Human Services, Public Health Services, National Institutes of Health, 1991), incorporated by reference.

TABLE II

Key framework residues targeted for diversification.

| | Position | Human | Rabbit | Diversification | |
|---|---|---|---|---|---|
| V$_L$ | 43 | A | P | A | V |
| | 46 | L | F | L | F |
| | 71 | F | Y | F | Y |
| | 80 | P | A | P | A |
| V$_H$ | 27 | F | I | F | I |
| | 28 | T | D | T | D |
| | 71 | R | L | R | L |
| | 75 | K | Q | K | Q |
| | 78 | L | V | L | V |
| | 91 | Y | F | Y | F |

Linked positions (VH 27–28 and VH 71–75, respectively) indicate a coupled diversification that limits the selection to either all-human or all rabbit sequence.

Overlapping oligonucleotides were designed, synthesized, and then assembled to create synthetic V$_\lambda$ and V coding sequences, using PCR. The procedure described, supra, for the generation of rabbit antibody library was followed, and when the final constructs were completed, they were Sfi I cloned into a vector carrying a chloramphenicol resistence gene, to avoid contamination with phage from the rabbit antibody. The resulting library consisted of 1×10$^7$ independent transformants with a theoretical complexity of 2×10$^7$.

The following oligonucleotides were used for humanization, L denotes primers for the V$_L$ assembly, H denotes primers for the V$_H$ assembly:

L1,
5'-gagctccaga tgacccagtc tccatcctcc ctgtctgcat ctgtaggaga cagagtcacc atcacttgcc tggccagtga gttccttttt aatggtgtat cc-3';(SEQ ID NO:23)

L2,
5'-agatgggacc ccagattcta aattggatgc accatagatc aggarcttag garctttccc tggtttctgc tgataccagg atacaccatt aaaaaggaac tc-3'; (SEQ ID NO:24)

L3,
5'-aatttagaat ctggggtccc atctcggttc agtggcagtg gatctgggac agattwcact ctcaccatca gcagcctgca gsctgaagat gttgcaact-3'; (SEQ ID NO:25)

L4,
5'-ttttgatctcc accttggtcc ctccgccgaa agtcaaacca ctactaccac tataaccgcc tagacagtaa taagttgcaa catcttcags ctgcag-3' (SEQ ID NO:26)

L flank sense,
5'-gaggaggagg aggagggccc aggcggccga gctccagatg acccagtctc ca-3';(SEQ ID NO:27)

L antisense flank,
5'-gacagatggt gcagccacag ttcgtttgat ctccaccttg gtccctcc-3'; (SEQ ID NO:28)

H1,
5'-gaggtgcagc tggtggagtc tgggggaggc ctggtcaagc ctgggggtc cctgagactc tcctgtgcag cctctgga-3';(SEQ ID NO:29)

H2A,
5'-ccagctaatg ccatagtgac tgaaggtgaa tccagaggct gcacaggaga gtct-3';(SEQ ID NO:30)

H2B,
5'-ccagctaatg ccatagtgac tgaagtcgat tccagaggct gcacaggaga gtct-3';(SEQ ID NO:31)

H3,
5'-ttcagtcact atggcattag ctgggtccgc caggctccag ggaaggggct ggagtgggtc gcctacattt atcctaatta tgggagtgta gactacgcga gc-3';(SEQ ID NO:32)

H4A,
5'-gttcatttgc agatacastg agttcttggc gttgtctctg gagatggtga atcggccatt cacgctgctc gcgtagtcta cactcccata-3'; (SEQ ID NO:33)

H4B,
5'-gttcatttgc agatacastg agttctgggc gttgtcgagg gagatggtga atcggccatt cacgctgctc gcgtagtcta cactcccata-3'; (SEQ ID NO:34)

H5,
5'-aactcastgt atctgcaaat gaacagcctg agagccgagg acacggccgt atattwctgt gcgagagatc ggggttatta ttctggtagt-3'; (SEQ ID NO:35)

H6,
5'-tgaggagacg gtgaccaggg tgccctggcc ccagagatcc aaccgagtcc ccctactacc agaataataa ccccgatc-3';(SEQ ID NO:36)

H flank sense,
51'-gctgcccaac cagccatggc cgaggtgcag ctggtggagt ctggggga-3'; (SEQ ID NO:37)

H flank antisense,
5'-gaccgatggg ccttggtgg aggctgagga gacggtgacc agggtgcc-3'.(SEQ ID NO:38)

The transformants were panned as described supra, but the amount of antigen employed was decreased over the course of panning. In the first two rounds, 100 ng were used, followed by two rounds at 50 ng, and two rounds at 25 ng. Ten washing steps were carried out for each round, using 0.5% (v/v) Tween 20 in TBS. Rounds 3 and 4, and rounds 5 and 6, were linked without phage amplification. To do this, phages from rounds 3 and 5 were eluted, using 50 µl of 100 mM HCl-glycine (pH 2.2), incubated for 10 minutes at room temperature, collected, neutralized with 3 µl of 2M Tris base, and 50 µl of 1% (w/v) BSA in TBS. The phages were than directly subjected to another round of panning. Phages from rounds 1, 2, 4 and 6 were eluted by trypsinization, as described supra.

Seventy clones resulted from final output. All were found to be positive via ELISA. Twenty-four of the seventy clones were further analyzed via DNA sequencing.

Sequences for the heavy and light chain of 6 of these clones (total of 12 sequences) are presented as human VLA, VLB, VLC, VLD, VLE, VLF, VHA, VHB, VHC, VHD, VHE, VHF in FIG. 1. A consensus sequence was found for the diversified framework of V$_H$, with positions 27 and 28 in framework 1, and positions 71 and 75 in framework 3 being found to contain original rabbit residues isoleucine, aspartic acid, leucine, and glutamine, respectively, in 16 of 24 clones. Three clones contained human residues phenylalanine and threonine at positions 27 and 28, and none contained human residues at positions 71 and 75. Two of the diversified positions contained mutations. Both appeared to be due to a single point mutation, probably generated via misincorporation during oligonucleotide synthesis, or assembly. Three clones had glycine at position 28, and phenylalanine was found in two clones at position 71. These 5 clones, notably, demonstrated the strongest reactivity in ELISA. The two remaining diversified positions in the framework, i.e., positions 78 and 91, did not give significant consensus sequence, but random selection of human/rabbit residues. This was also the case for 3 of 4 diversified positions in the V$_\lambda$ framework (positions 43 and 46 in framework 2, positron 71 in framework 3). Proline, a human residue, was found at position 80 in framework 3, in 18 of 24 clones, including the 5 mutated clones showing strongest reactivity via ELISA.

The six clones (human A to F, wherein each comprise a VH and VL as shown in FIG. 1) referred to supra were then produced as soluble Fab molecules via E.coli, and purified as described supra. Yields ranged from 0.5 to 2 mg per 1 liter shake flask culture. When subjected to flow cytometry, all Fabs bound to cells expressing native A33 antigen. Those cells which did not express human A33 were not recognized.

There were slight differences in fluorescence intensity, which correlated to differences in affinity to immobilized recombinant human A33, measured by surface plasmon resonance carried out as described supra. This suggests strongly that the antibodies, which were selected on immobilized, recombinant antigen, bind to a native epitope fully accessible on the cell surface, thereby constituting a relevant therapeutic target.

EXAMPLE 6
Characterization of Novel A33 Antibodies

Preparation of recombinant A33 antigen: A 1.6 kb XhoI/PstI cDNA fragment, containing the full length coding sequence of A33, was subcloned into pBlueBac4 transfer vector. To generate the transfer vector harboring only extracellular domain of A33 (ECD-A33) the 340bp BglII/PstI fragment was removed from the pBlueBac4/A33 vector and the resulting plasmid was religated with the use of two overlapping oligonucleotides (gatctccctccatgaaccat catcatcatcatcattgactgca SEQ ID NO:127) and gtcaatgatgatgatgatgatggttcatggaggga (SEQ ID NO:128). When annealed, these oligonucleotides would create BglII and PstI sites at the 5' and 3' end respectively and sequences encoding SPSMHH-HHHH (SEQ ID NO:129) (SEQ ID NO:128) and stop codon between both restriction sites. Transfection of Sf9 cells with pBlueBac4/A33 and pBlueBac4/A33-ECD transfer vectors and isolation of recombinant viruses was performed according to the manufacturer's recommendations (Invitrogen). For large-scale expression, Sf9 cells were infected with the recombinant viruses at a multiplicity of infection (MOI) of 10. After three days of infection cells were harvested by centrifugation and used immediately for the purification of recombinant proteins. Expressed protein was purified by immunoaffinity chromatography using mouse mAb A33 immobilized to protein A conjugated Sepharose 4B beads with dimethylpimelimidate as previously described (Moritz, R. L. et al., J. Chromatogr. A, 798: 91–101).

Western Blots: Triton X-100 (0.3% in PBS pH 7.5) lysates of colon cancer cells were resolved by SDS-PAGE on 10–20% polyacrylamide Tris-glycine pre-cast gels under reducing (5% β-ME) and non-reducing conditions. Proteins were blotted to PVDF and incubated with 0.5 ug/ml murine A33 mAb or humanized Fab B overnight at 4° C. Specific binding was detected by alkaline phosphatase conjugated species specific secondary Abs and visualized using chemiluminescent detection. Blocking and washing steps were carried out as per manufacturer's instructions.

Hemadsorption assay: The protein A, rabbit anti-human F(ab')$_2$ mixed hemadsorption assay which detects surface bound Fab by adherence of protein A coated human RBC (blood group O) to target cells was performed as previously described (Pfreundschuh, M. et al., Proc. Natl. Acad. Sci. (Wash.), 75, 5122–5126 (1978)).

Results: Fabs A, B, C, E, and F were analyzed for reactivity with A33 antigen extracted from colon cancer cell lines by Western blot assays (FIG. 2). All new Fabs reacted with a band of about 43 kD protein under non reducing conditions. No Western blot reactivity was observed using reducing conditions (FIG. 2). These Western blot reactivities of the Fabs prepared from a rabbit phage display library are identical with those obtained with mouse mAb A33 suggesting recognition of a conformational epitope on the A33 antigen as previously described for mAb A33 (Catimel, B. et al., J. Biol. Chem. 271:25664–25670).

Mixed hemadsorption assays: Fabs A, B, C, E, and F were analyzed for reactivity with A33 antigen expressed on the cell surface of human cancer cell lines using a mixed hemadsorption assay. All five Fabs bound to A33+but not to A33− cancer cells (listed below). Fabs A and B showed the strongest reactivity with cell surface expressed A33 antigen. Mixed Hemadsorption Titer (ng Ig/ml)

TABLE III

| Ig | L1M1215 | SW1222 | NCI-H508 | HT29 | SW620 |
|---|---|---|---|---|---|
| Fab A | 10# | 1 | 5 | — | — |
| Fab B | 10 | 5 | 10 | — | — |
| Fab C | 80 | nd | nd | — | — |
| Fab E | 40 | 20 | 20 | — | — |
| Fab F | 10 | 20 | 20 | — | — |
| HmAbA33 | 5 | 5 | 5 | — | — |

Lowest concentration of Fab or human mAb A33 giving 50% rosetting.
nd = not determined.

The difference between the humanized clones were found to correlate with their differences in affinity to immobilized recombinant human A33 antigen. The humanized Fab were further analyzed for reactivity with human A33 antigen extracted from colon cancer cell lines by Western blotting. As shown for humanized clone B (FIG. 2), the humanized Fab strongly reacted with a band of about 43 kD under nonreducing conditions. No reactivity was observed using reducing condition, suggesting the recognition of a conformation epitope on human A33 antigen (Catimel, B. et al., (1996) J. Biol. Chem. 271, 25664–25670). Taken together, these results demonstrate that the selected humanized antibodies bind to a native epitope on human A33 antigen that is fully accessible on the cell surface.

EXAMPLE 7
Immunohistochemistry

In order to evaluate the selectivity of the humanized Fab in an independent system of higher complexity, their reactivity with tumor tissue sections was analyzed by immunohistochemistry. All immnunochemical stainings were done on snap-frozen tissue samples, embedded in O.C.T. compound (Tissue Tek, Torrance, Calif.) 0.5 $\mu$m cuts (HM503 cryostat, Zeiss, Walldorf, Germany) were mounted on slides for immunohistochemistry (Superfrost Plus, Fisher Scientific, Pittsburgh, Pa.). Serial sections were used, so as to compare staining results of the different antibody preparations. After cutting, the slides were fixed in cold acetone for 10 min and then air dried. Reactivity of the humanized Fab was analyzed using the colon cancer cell line SW1222 xenografted into nude mice. A working concentration of Fab (1 pg/ml) was established by titering. The humanized Fab was detected by biotinylated goat-anti human F(ab)$_2$ polyclonal antibodies (1:200; Vector, Burlingame, Calif.) and an avidin-biotin-complex system (ABC/Elite kit, Vector). Diaminobenzidine tetrahydrochloride (DAB, Biogenex, San Ramon, Calif.) was used as a chromogen. Reactivity of the humanized Fab was also evaluated in human colonic adenocarcinoma samples. In order to prevent immunoreactivity of endogenous human immunoglobulin, a special technique for the detection of humanized Fab was utilized. Prior to addition to tissue, the humanized Fab (1 $\mu$g/ml) was incubated with biotinylated goat-anti human F(ab)$_2$ polyclonal antibodies in a test tube. The optimal ratio of humanized Fab to secondary antibody was determined in separate titration assays. Incubation of humanized Fab and secondary antibody was done at room temperature for 1 hour and followed by an addition of human serum in order to block the activity of unbound secondary antibody. Again, the optimal ratio of human serum to secondary antibody was determined in separate titration assays.

Figure 7A:
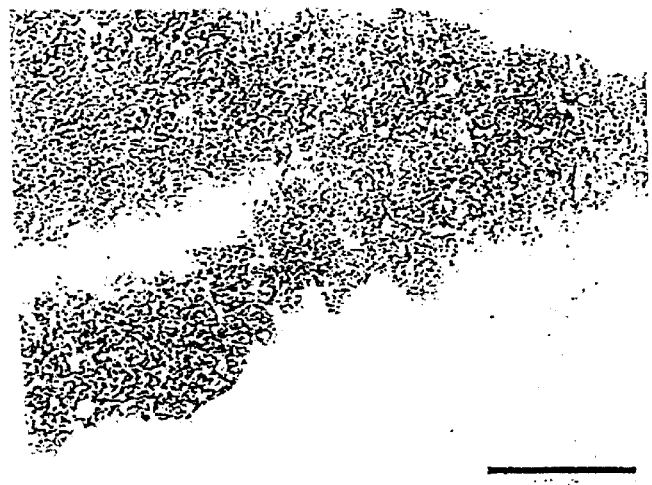
FIG. 7 Immunohistochemical reactivity of humanized Fab B in human colon cancer tissue sections. A and B, xenograft of human colon cancer cell line SW 1222 in nude mice, C–F, serial sections of moderately differentiated human colon adenocarcinoma. Scale bar=300 µm. Specific binding was detected by biotinylated goat-anti human F(ab')$_2$ polyclonal antibodies and visualized using an avidin-biotin-complex system and diaminobenzidine tetrahydrochloride as a chromogen. (A) Humanized Fab B showed intense staining in SW1222 xenograph. (B) Buffer only without application of humanized Fab (negative control) showing no staining in SW 1222 xenograft. (C) Mouse monoclonal antibody A33 showing intense staining of dysplastic glandular structures in human colon adenocarcinoma. (D) Humanized Fab B revealing similar staining in corresponding carcinoma areas after blocking of endogenous human immunoglobulins. No staining of additional tissue components due to endogenous human immunoglobulins is detectable. (E) Buffer only without application of humanized Fab (negative control) but with blocking of endogenous human immunoglobulins showing no staining. (F) Buffer only without application of humanized Fab (negative control) and omitting the blocking of endogenous human immunoglobulins showing intense staining of endogenous human immunoglobulins.
Figure 7B:
Figure 7C:
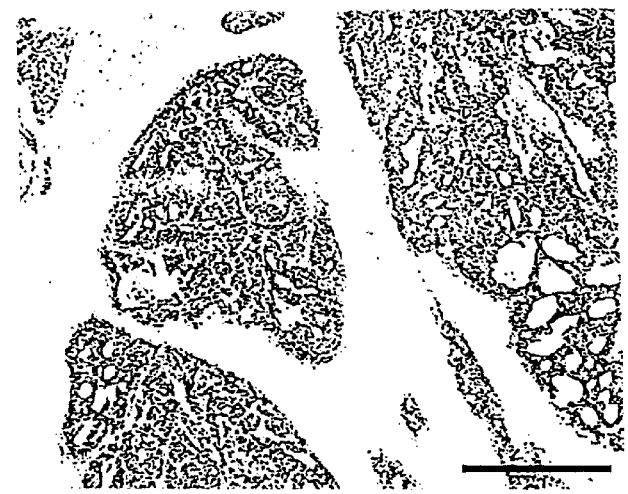
Figure 7D:
Figure 7E:
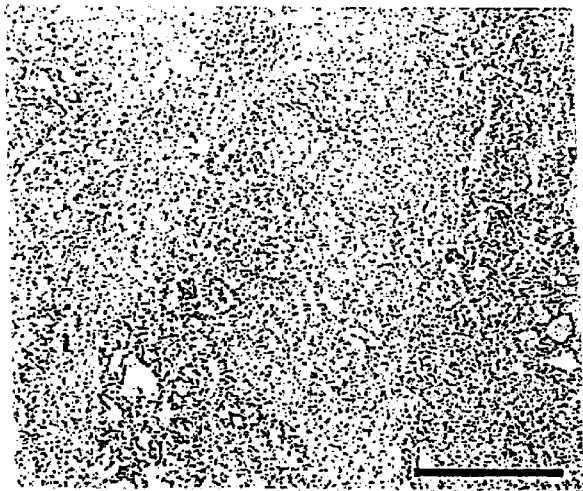
Figure 7F:

As can be seen in FIG. 7, the humanized Fab reacted strongly with xenografts of the human colon cancer cell line SW1222 grown in nude mice (FIGS. 7A and 7B). The humanized Fab revealed immunoreactivity similar to the mouse monoclonal antibody A33 with an intense staining of dysplastic glandular structures in tissue sections of human colon adenocarcinoma after blocking endogenous human immunoglobulins (FIGS. 7C and 7D). A comparison of corresponding tissue sections stained with the full blocking step and stained without blocking of the endogenous human immunoglobulins illustrates the amount of internal reactivity (FIG. 7F) and its complete blocking (FIG. 7E).

The terms and expressions which have been employed are used as terms of description and not of limitation, and there is no intention in the use of such terms and expressions of excluding any equivalents of the features shown and described or portions thereof, it being recognized that various modifications are possible within the scope of the invention. All references cited are herein incorporated by reference.

What is claimed is:

1. A method of reducing the effects of a cancer that expresses A33 antigen in a subject comprising administering to said subject a pharmaceutically effective amount of an anti-cancer agent conjugated to an immunoglobulin molecule, wherein said immunoglobulin molecule binds with specificity to A33 antigen and comprises six complementarity determining regions (CDRs) the amino acid sequences of which selected from the group consisting of:

(i) SEQ ID NO.: 68 or SEQ ID NO.: 69 ($V_L$CDR1);
(ii) SEQ ID NO.: 70 or SEQ ID NO.: 71 ($V_L$CDR2);
(iii) SEQ ID NO.: 72 or SEQ ID NO.: 73 ($V_L$CDR3);
(iv) SEQ ID NO.: 74 or SEQ ID NO.: 75 ($V_H$CDR1);
(v) SEQ ID NO.: 76, SEQ ID NO.: 77 or SEQ ID NO.: 78 ($V_H$CDR2); and
(vi) SEQ ID NO.: 79 or SEQ ID NO.: 80 ($V_H$CDR3), wherein (i), (ii), (iii), (iv), (v), and (vi) are present in said immunoglobulin molecule sufficient to reduce effect of said cancer that expresses A33 antigen.

2. The method of claim 1 wherein said immunoglobulin molecule is an antibody, an Fv fragment, an Fab fragment, a F(ab)$_2$ fragment, a single chain antibody, or a multimeric antibody.

3. The method of claim 1, wherein said immunoglobulin molecule is an IgM, IgD, IgG, IgA, or IgE molecule.

4. The method of claim 1, wherein said cancer is colon cancer or stomach cancer.

5. The method of claim 1 wherein said immunoglobulin molecule is a humanized antibody.

6. The method of claim 1, wherein the immunoglobulin molecule binds A33 antigen with an affinity which is stronger than 500 pM.

7. The method of claim 1, wherein the immunoglobulin molecule binds A33 antigen with an affinity which is stronger than 100 pM.

8. The method of claim 1, wherein the immunoglobulin molecule is a protein of the immunoglobulin gene superfamily.

9. The method of claim 1, wherein the $V_L$CDR regions of said immunoglobulin molecule comprise SEQ ID NO.: 68, SEQ ID NO.: 70, and SEQ ID NO.: 72.

10. The method of claim 1, wherein the $V_H$CDR regions of said immunoglobulin molecule comprise SEQ ID NO.: 74, SEQ ID NO.: 76, and SEQ ID NO.: 79.

11. The method of claim 1, wherein the $V_L$CDR regions of said immunoglobulin molecule comprise SEQ ID NOS.: 68, 70, and 72, and the $V_H$CDR regions comprise SEQ ID NOS.: 74, 76, and 79.

12. The method of claim 1, wherein said immunoglobulin molecule further comprises $V_L$FR1, the amino acid sequence of which is selected from the group consisting of SEQ ID NO.: 81, 82, 83 or 84; $V_L$FR2, the amino acid sequence of which is selected from the group consisting of SEQ ID NO.: 85, 86, 87, 88, 89, 90 or 91; $V_L$FR3, the amino acid sequence of which is set forth at SEQ ID NO.: 92, 93, 94, 95 or 96; and $V_L$FR4, the amino acid sequence of which is set forth at SEQ ID NO.: 97 or 98.

13. The method of claim 1, wherein said immunoglobulin molecule further comprises $V_H$FR1, the amino acid sequence of which is selected from the group consisting of SEQ ID NOS.: 99, 100, 101, 102, 103 and 104; $V_H$FR2, the amino acid sequence of which is selected from the group consisting of SEQ ID NOS.: 105, 106, and 107; $V_H$FR3, the amino acid sequence of which is selected from the group consisting of SEQ ID NOS.: 108, 109, 110, 111, 112, 113, 114, 115, 116, 117, 118, 119, 120, 121, 122, 123, and 124; and $V_H$FR4, the amino acid sequence of which is selected from the group consisting of SEQ ID NOS.: 125 and 126.

14. The method of claim 1, wherein the immunoglobulin molecule which binds specifically to A33 antigen, comprises;

$V_L$CDR1: SEQ ID NO.: 68
$V_L$CDR2: SEQ ID NO.: 70
$V_L$CDR3: SEQ ID NO.: 72
$V_H$CDR1: SEQ ID NO.: 74
$V_H$CDR2: SEQ ID NO.: 76
$V_H$CDR3: SEQ ID NO.: 79
$V_L$FR1: SEQ ID NO.: 81
$V_L$FR2: SEQ ID NO.: 87
$V_L$FR3: SEQ ID NO.: 92
$V_L$FR4: SEQ ID NO.: 97
$V_H$FR1: SEQ ID NO.: 101
$V_H$FR2: SEQ ID NO.: 107
$V_H$FR3: SEQ ID NO.: 110, and
$V_H$FR4: SEQ ID NO.: 126.

15. The method of claim 1, wherein the light chain of said immunoglobulin molecule, is selected from the group consisting of SEQ ID NOS.: 20, 21, 22, 39, 40, 41, 42, 43, 44 and 45, and the heavy chain is selected from the group consisting of SEQ ID NOS.: 46, 47, 48, 49, 50, 51 52, 53, 54, 55, 56, 57, 58, 59, 60, 61, 62, 63, 64, 65, 66 and 67.

16. The method of claim 1, wherein the light chain of said immunoglobulin molecule of claim 12, is selected from the group consisting of SEQ ID NOS.: 39, 40, 41, 42, 43, 44 and 45, and the heavy chain is selected from the group consisting of SEQ ID NOS.: 49, 50, 51, 52, 53, 54, 55, 56, 57, 58, 59, 60, 61, 62, 63, 64, 65, 66 and 67.

17. The method of claim 1, wherein the immunoglobulin molecule has (i) the light chain set forth in SEQ ID NO.: 39 and the heavy chain set forth in SEQ ID NO.: 50, (ii) the light chain set forth in SEQ ID NO.: 40 and the heavy chain set forth in SEQ ID NO.: 51, (iii) the light chain set forth in SEQ ID NO.: 41 and the heavy chain set forth in SEQ ID NO.: 52, (iv) the light chain set forth in SEQ ID NO.: 42 and the heavy chain set forth in SEQ ID NO.: 53, (v) the light chain set forth in SEQ ID NO.: 43 and the heavy chain set forth in SEQ ID NO.: 54, and (vi) the light chain set forth in SEQ ID NO.: 44 and the heavy chain set forth in SEQ ID NO.: 55.

18. The method of claim 1, wherein said anti-cancer agent is a drug selected from the group consisting of calicheamicin, QFA, BCNU, streptozoicin, vincristine and 5-fluorouracil.

19. The method of claim 1, wherein said anti-cancer agent is selected from the group consisting of a cytotoxic agent, a chemotherapeutic agent, a cytokine, and a radioactive isotope.

* * * * *

SEQUENCE LISTING

```
<160> NUMBER OF SEQ ID NOS:    129

<210> SEQ ID NO 1
<211> LENGTH: 38
<212> TYPE: DNA
<213> ORGANISM: Homo sapiens
<220> FEATURE:

<400> SEQUENCE: 1
gggcccaggc ggccgagctc gtgmtgaccc agactcca                                38

<210> SEQ ID NO 2
<211> LENGTH: 38
<212> TYPE: DNA
<213> ORGANISM: Homo sapiens
<220> FEATURE:

<400> SEQUENCE: 2
gggcccaggc ggccgagctc gatmtgaccc agactcca                                38

<210> SEQ ID NO 3
<211> LENGTH: 38
<212> TYPE: DNA
<213> ORGANISM: Homo sapiens
<220> FEATURE:

<400> SEQUENCE: 3
gggcccaggc ggccgagctc gtgatgaccc agactgaa                                38

<210> SEQ ID NO 4
<211> LENGTH: 41
<212> TYPE: DNA
<213> ORGANISM: Homo sapiens
<220> FEATURE:

<400> SEQUENCE: 4
acagatggtg cagccacagt taggatctcc agctcggtcc c                            41

<210> SEQ ID NO 5
<211> LENGTH: 42
<212> TYPE: DNA
<213> ORGANISM: Homo sapiens
<220> FEATURE:

<400> SEQUENCE: 5
gacagatggt gcagccacag ttttgatttc cacattggtg cc                           42

<210> SEQ ID NO 6
<211> LENGTH: 42
<212> TYPE: DNA
<213> ORGANISM: Homo sapiens
```

-continued

<220> FEATURE:

<400> SEQUENCE: 6
gacagatggt gcagccacag ttttgacsac cacctcggtc cc                          42

<210> SEQ ID NO 7
<211> LENGTH: 40
<212> TYPE: DNA
<213> ORGANISM: Homo sapiens
<220> FEATURE:

<400> SEQUENCE: 7
gggcccaggc ggccgagctc gtgctgactc agtcgccctc                              40

<210> SEQ ID NO 8
<211> LENGTH: 45
<212> TYPE: DNA
<213> ORGANISM: Homo sapiens
<220> FEATURE:

<400> SEQUENCE: 8
cgagggggca gccttgggct ggcctgtgac ggtcagctgg gtccc                        45

<210> SEQ ID NO 9
<211> LENGTH: 42
<212> TYPE: DNA
<213> ORGANISM: Homo sapiens
<220> FEATURE:

<400> SEQUENCE: 9
gctgcccaac cagccatggc ccagtcggtg gaggagtccr gg                           42

<210> SEQ ID NO 10
<211> LENGTH: 42
<212> TYPE: DNA
<213> ORGANISM: Homo sapiens
<220> FEATURE:

<400> SEQUENCE: 10
gctgcccaac cagccatggc ccagtcggtg aaggagtccg ag                           42

<210> SEQ ID NO 11
<211> LENGTH: 42
<212> TYPE: DNA
<213> ORGANISM: Homo sapiens
<220> FEATURE:

<400> SEQUENCE: 11
gctgcccaac cagccatggc ccagtcgytg gaggagtccg gg                           42

<210> SEQ ID NO 12
<211> LENGTH: 44
<212> TYPE: DNA
<213> ORGANISM: Homo sapiens
<220> FEATURE:

<400> SEQUENCE: 12
gctgcccaac cagccatggc ccagsagcag ctgrtggagt ccgg                         44

<210> SEQ ID NO 13
<211> LENGTH: 45
<212> TYPE: DNA
<213> ORGANISM: Homo sapiens
<220> FEATURE:

-continued

```
<400> SEQUENCE: 13
cgatgggccc ttggtggagg ctgargagay ggtgaccagg gtgcc                          45

<210> SEQ ID NO 14
<211> LENGTH: 41
<212> TYPE: DNA
<213> ORGANISM: Homo sapiens
<220> FEATURE:

<400> SEQUENCE: 14
gaggaggagg aggaggaggc ggggcccagg cggccgagct c                              41

<210> SEQ ID NO 15
<211> LENGTH: 20
<212> TYPE: DNA
<213> ORGANISM: Homo sapiens
<220> FEATURE:

<400> SEQUENCE: 15
gccatggctg gttgggcagc                                                      20

<210> SEQ ID NO 16
<211> LENGTH: 21
<212> TYPE: DNA
<213> ORGANISM: Homo sapiens
<220> FEATURE:

<400> SEQUENCE: 16
gctgcccaac cagccatggc c                                                    21

<210> SEQ ID NO 17
<211> LENGTH: 39
<212> TYPE: DNA
<213> ORGANISM: Homo sapiens
<220> FEATURE:

<400> SEQUENCE: 17
gaggaggagg aggaggagag aagcgtagtc cggaacgtc                                 39

<210> SEQ ID NO 18
<211> LENGTH: 23
<212> TYPE: DNA
<213> ORGANISM: Homo sapiens
<220> FEATURE:

<400> SEQUENCE: 18
aagacagcta tcgcgaattg cac                                                  23

<210> SEQ ID NO 19
<211> LENGTH: 24
<212> TYPE: DNA
<213> ORGANISM: Homo sapiens
<220> FEATURE:

<400> SEQUENCE: 19 gccccttat tagcctttgc catc                                                  24

<210> SEQ ID NO 20
<211> LENGTH: 109
<212> TYPE: PRT
<213> ORGANISM: Homo sapiens
<220> FEATURE:

<400> SEQUENCE: 20
```

```
Glu Phe Asp Met Thr Gln Thr Pro Pro Ser Leu Ser Ala Ser Val Gly
                 5                  10                  15

Glu Thr Val Arg Ile Arg Cys Leu Ala Ser Glu Phe Leu Phe Asn Gly
             20                  25                  30

Val Ser Trp Tyr Gln Gln Lys Pro Gly Lys Pro Lys Phe Leu Ile
         35                  40                  45

Ser Gly Ala Ser Asn Leu Glu Ser Gly Val Pro Arg Phe Ser Gly
 50                  55                  60

Ser Gly Ser Gly Thr Asp Tyr Thr Leu Thr Ile Gly Gly Val Gln Ala
65                   70                  75                  80

Glu Asp Val Ala Thr Tyr Tyr Cys Leu Gly Gly Tyr Ser Gly Ser Ser
                 85                  90                  95

Gly Leu Thr Phe Gly Ala Gly Thr Asn Val Glu Ile Lys
            100                 105
```

<210> SEQ ID NO 21
<211> LENGTH: 109
<212> TYPE: PRT
<213> ORGANISM: Homo sapiens
<220> FEATURE:

<400> SEQUENCE: 21

```
Glu Leu Val Met Thr Gln Thr Pro Pro Ser Leu Ser Ala Ser Val Gly
                 5                  10                  15

Glu Thr Val Arg Ile Arg Cys Leu Ala Ser Glu Phe Leu Phe Asn Gly
             20                  25                  30

Val Ser Trp Tyr Gln Gln Lys Pro Gly Lys Pro Lys Phe Leu Ile
         35                  40                  45

Ser Gly Ala Ser Asn Leu Glu Ser Gly Val Pro Arg Phe Ser Gly
 50                  55                  60

Ser Gly Ser Gly Thr Asp Tyr Thr Leu Thr Ile Gly Gly Val Gln Ala
65                   70                  75                  80

Glu Asp Val Ala Thr Tyr Tyr Cys Leu Gly Gly Tyr Ser Gly Ser Ser
                 85                  90                  95

Gly Leu Thr Phe Gly Ala Gly Thr Asn Val Glu Ile Lys
            100                 105
```

<210> SEQ ID NO 22
<211> LENGTH: 109
<212> TYPE: PRT
<213> ORGANISM: Homo sapiens
<220> FEATURE:

<400> SEQUENCE: 22

```
Glu Leu Val Leu Thr Gln Thr Pro Pro Ser Leu Ser Pro Ser Val Gly
                 5                  10                  15

Glu Thr Val Arg Ile Arg Cys Leu Ala Ser Asp Phe Leu Phe Asn Gly
             20                  25                  30

Val Ser Trp Tyr Gln Gln Lys Pro Glu Lys Pro Pro Thr Leu Leu Ile
         35                  40                  45

Ser Gly Ala Ser Asp Leu Glu Thr Gly Val Pro Arg Phe Ser Gly
 50                  55                  60

Ser Gly Ser Gly Thr Asp Tyr Thr Leu Thr Ile Gly Gly Val Gln Ala
65                   70                  75                  80

Glu Asp Ala Ala Thr Tyr Tyr Cys Leu Gly Gly Tyr Ser Gly Ser Ala
                 85                  90                  95

Gly Leu Thr Phe Gly Ala Gly Thr Asn Val Glu Ile Lys
```

-continued

<210> SEQ ID NO 23
<211> LENGTH: 102
<212> TYPE: DNA
<213> ORGANISM: Homo sapiens
<220> FEATURE:

<400> SEQUENCE: 23
gagctccaga tgacccagtc tccatcctcc ctgtctgcat ctgtaggaga cagagtcacc      60
atcacttgcc tggccagtga gttcctttttt aatggtgtat cc                        102

<210> SEQ ID NO 24
<211> LENGTH: 102
<212> TYPE: DNA
<213> ORGANISM: Homo sapiens
<220> FEATURE:

<400> SEQUENCE: 24
agatgggacc ccagattcta aattggatgc accatagatc aggarcttag garctttccc      60
tggtttctgc tgataccagg atacaccatt aaaaaggaac tc                         102

<210> SEQ ID NO 25
<211> LENGTH: 99
<212> TYPE: DNA
<213> ORGANISM: Homo sapiens
<220> FEATURE:

<400> SEQUENCE: 25
aatttagaat ctggggtccc atctcggttc agtggcagtg gatctgggac agattwcact      60
ctcaccatca gcagcctgca gsctgaagat gttgcaact                             99

<210> SEQ ID NO 26
<211> LENGTH: 96
<212> TYPE: DNA
<213> ORGANISM: Homo sapiens
<220> FEATURE:

<400> SEQUENCE: 26
tttgatctcc accttggtcc ctccgccgaa agtcaaacca ctactaccac tataaccgcc      60
tagacagtaa taagttgcaa catcttcags ctgcag                                96

<210> SEQ ID NO 27
<211> LENGTH: 52
<212> TYPE: DNA
<213> ORGANISM: Homo sapiens
<220> FEATURE:

<400> SEQUENCE: 27
gaggaggagg aggagggccc aggcggccga gctccagatg acccagtctc ca              52

<210> SEQ ID NO 28
<211> LENGTH: 48
<212> TYPE: DNA
<213> ORGANISM: Homo sapiens
<220> FEATURE:

<400> SEQUENCE: 28
gacagatggt gcagccacag ttcgtttgat ctccaccttg gtccctcc                   48

<210> SEQ ID NO 29
<211> LENGTH: 78

<212> TYPE: DNA
<213> ORGANISM: Homo sapiens
<220> FEATURE:

<400> SEQUENCE: 29
gaggtgcagc tggtggagtc tgggggaggc ctggtcaagc ctgggggtc cctgagactc    60 tcctgtgcag cctctgga                                                 78

<210> SEQ ID NO 30
<211> LENGTH: 54
<212> TYPE: DNA
<213> ORGANISM: Homo sapiens
<220> FEATURE:

<400> SEQUENCE: 30
ccagctaatg ccatagtgac tgaaggtgaa tccagaggct gcacaggaga gtct          54

<210> SEQ ID NO 31
<211> LENGTH: 54
<212> TYPE: DNA
<213> ORGANISM: Homo sapiens
<220> FEATURE:

<400> SEQUENCE: 31
ccagctaatg ccatagtgac tgaagtcgat tccagaggct gcacaggaga gtct          54

<210> SEQ ID NO 32
<211> LENGTH: 102
<212> TYPE: DNA
<213> ORGANISM: Homo sapiens
<220> FEATURE:

<400> SEQUENCE: 32
ttcagtcact atggcattag ctgggtccgc caggctccag ggaagggct ggagtgggtc    60 gcctacattt atcctaatta tgggagtgta gactacgcga gc                     102

<210> SEQ ID NO 33
<211> LENGTH: 90
<212> TYPE: DNA
<213> ORGANISM: Homo sapiens
<220> FEATURE:

<400> SEQUENCE: 33
gttcatttgc agatacastg agttcttggc gttgtctctg agatggtga atcggccatt    60 cacgctgctc gcgtagtcta cactcccata                                    90

<210> SEQ ID NO 34
<211> LENGTH: 90
<212> TYPE: DNA
<213> ORGANISM: Homo sapiens
<220> FEATURE:

<400> SEQUENCE: 34
gttcatttgc agatacastg agttctgggc gttgtcgagg gagatggtga atcggccatt   60
cacgctgctc gcgtagtcta cactcccata                                    90

<210> SEQ ID NO 35
<211> LENGTH: 90
<212> TYPE: DNA
<213> ORGANISM: Homo sapiens
<220> FEATURE:

<400> SEQUENCE: 35

```
aactcastgt atctgcaaat gaacagcctg agagccgagg cacggccgt atattwctgt      60 gcgagagatc ggggttatta ttctggtagt                                      90
```

<210> SEQ ID NO 36
<211> LENGTH: 78
<212> TYPE: DNA
<213> ORGANISM: Homo sapiens
<220> FEATURE:

<400> SEQUENCE: 36

```
tgaggagacg gtgaccaggg tgccctggcc ccagagatcc aaccgagtcc ccctactacc     60
agaataataa ccccgatc                                                   78
```

<210> SEQ ID NO 37
<211> LENGTH: 48
<212> TYPE: DNA
<213> ORGANISM: Homo sapiens
<220> FEATURE:

<400> SEQUENCE: 37

```
gctgcccaac cagccatggc cgaggtgcag ctggtggagt ctggggga                  48
```

<210> SEQ ID NO 38
<211> LENGTH: 48
<212> TYPE: DNA
<213> ORGANISM: Homo sapiens
<220> FEATURE:

<400> SEQUENCE: 38

```
gaccgatggg cccttggtgg aggctgagga gacggtgacc aggtgcc                   48
```

<210> SEQ ID NO 39
<211> LENGTH: 109
<212> TYPE: PRT
<213> ORGANISM: Homo sapiens
<220> FEATURE:

<400> SEQUENCE: 39

```
Glu Leu Gln Met Thr Gln Ser Pro Ser Ser Leu Ser Ala Ser Val Gly
                5                   10                  15

Asp Arg Val Thr Ile Thr Cys Leu Ala Ser Glu Phe Leu Phe Asn Gly
            20                  25                  30

Val Ser Trp Tyr Gln Gln Lys Pro Gly Lys Val Pro Lys Phe Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Leu Gly Gly Tyr Ser Gly Ser Ser
                85                  90                  95

Gly Leu Thr Phe Gly Gly Gly Thr Lys Val Glu Ile Lys
                100                 105
```

<210> SEQ ID NO 40
<211> LENGTH: 109
<212> TYPE: PRT
<213> ORGANISM: Homo sapiens
<220> FEATURE:

<400> SEQUENCE: 40

Glu Leu Gln Met Thr Gln Ser Pro Ser Ser Leu Ser Ala Ser Val Gly
                5                   10                  15

Asp Arg Val Thr Ile Thr Cys Leu Ala Ser Glu Phe Leu Phe Asn Gly
            20                  25                  30

Val Ser Trp Tyr Gln Gln Lys Pro Gly Lys Val Pro Lys Phe Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Tyr Ser Gly Ser Ser
                85                  90                  95

Gly Leu Thr Phe Gly Gly Gly Thr Lys Val Glu Ile Lys
            100                 105

<210> SEQ ID NO 41
<211> LENGTH: 109
<212> TYPE: PRT
<213> ORGANISM: Homo sapiens
<220> FEATURE:

<400> SEQUENCE: 41

Glu Leu Gln Met Thr Gln Ser Pro Ser Ser Leu Ser Ala Ser Val Gly
                5                   10                  15

Asp Arg Val Thr Ile Thr Cys Leu Ala Ser Glu Phe Leu Phe Asn Gly
            20                  25                  30

Val Ser Trp Tyr Gln Gln Lys Pro Gly Lys Ala Pro Lys Phe Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Gly Tyr Ser Gly Ser Ser
                85                  90                  95

Gly Leu Thr Phe Gly Gly Gly Thr Lys Val Glu Ile Lys
            100                 105

<210> SEQ ID NO 42
<211> LENGTH: 109
<212> TYPE: PRT
<213> ORGANISM: Homo sapiens
<220> FEATURE:

<400> SEQUENCE: 42

Glu Leu Gln Met Thr Gln Ser Pro Ser Ser Leu Ser Ala Ser Val Gly
                5                   10                  15

Asp Arg Val Thr Ile Thr Cys Leu Ala Ser Glu Phe Leu Phe Asn Gly
            20                  25                  30

Val Ser Trp Tyr Gln Gln Lys Pro Gly Lys Val Pro Lys Phe Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Leu Gly Gly Tyr Ser Gly Ser Ser
                85                  90                  95

Gly Leu Thr Phe Gly Gly Gly Thr Lys Val Glu Ile Lys

```
                 100                 105

<210> SEQ ID NO 43
<211> LENGTH: 109
<212> TYPE: PRT
<213> ORGANISM: Homo sapiens
<220> FEATURE:

<400> SEQUENCE: 43

Glu Leu Gln Met Thr Gln Ser Pro Ser Ser Leu Ser Ala Ser Val Gly
                 5                  10                  15

Asp Arg Val Thr Ile Thr Cys Leu Ala Ser Glu Phe Leu Phe Asn Gly
             20                  25                  30

Val Ser Trp Tyr Gln Gln Lys Pro Gly Lys Ala Pro Lys Leu Leu Ile
         35                  40                  45

Tyr Gly Ala Ser Asn Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Leu Gly Tyr Ser Gly Ser Ser
                 85                  90                  95

Gly Leu Thr Phe Gly Gly Gly Thr Lys Val Glu Ile Lys
                 100                 105

<210> SEQ ID NO 44
<211> LENGTH: 109
<212> TYPE: PRT
<213> ORGANISM: Homo sapiens
<220> FEATURE:

<400> SEQUENCE: 44

Glu Leu Gln Met Thr Gln Ser Pro Ser Ser Leu Ser Ala Ser Val Gly
                 5                  10                  15

Asp Arg Val Thr Ile Thr Cys Leu Ala Ser Glu Phe Leu Phe Asn Gly
             20                  25                  30

Val Ser Trp Tyr Gln Gln Lys Pro Gly Lys Ala Pro Lys Phe Leu Ile
         35                  40                  45

Tyr Gly Ala Ser Asn Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gly Tyr Ser Gly Ser Ser
                 85                  90                  95

Gly Leu Thr Phe Gly Gly Gly Thr Lys Val Glu Ile Lys
                 100                 105

<210> SEQ ID NO 45
<211> LENGTH: 109
<212> TYPE: PRT
<213> ORGANISM: Homo sapiens
<220> FEATURE:

<400> SEQUENCE: 45

Glu Leu Gln Met Thr Gln Ser Pro Ser Ser Leu Ser Ala Ser Val Gly
                 5                  10                  15

Asp Arg Val Thr Ile Thr Cys Leu Ala Ser Glu Phe Leu Phe Asn Gly
             20                  25                  30

Val Ser Trp Tyr Gln Gln Lys Pro Gly Lys Ala Pro Lys Leu Leu Ile
         35                  40                  45
```

Tyr Gly Ala Ser Asn Leu Glu Ser Gly Val Pro Ser Arg Phe Ser Gly
                50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gly Gly Tyr Ser Gly Ser Ser
                    85                  90                  95

Gly Leu Thr Phe Gly Gly Gly Thr Lys Val Glu Ile Lys
                100                 105

<210> SEQ ID NO 46
<211> LENGTH: 124
<212> TYPE: PRT
<213> ORGANISM: Homo sapiens
<220> FEATURE:

<400> SEQUENCE: 46

Gln Gln Gln Val Met Glu Ser Gly Gly Gly Leu Val Thr Leu Gly Gly
                 5                  10                  15

Ser Leu Thr Leu Thr Cys Lys Ala Ser Gly Ile Asp Phe Ser Asn Asn
                20                  25                  30

Gly Ile Ser Trp Val Arg Gln Ala Pro Gly Lys Gly Leu Glu Trp Ile
             35                  40                  45

Leu Tyr Ile Tyr Pro Asp Tyr Gly Ser Thr Asp Tyr Ala Ser Trp Val
     50                  55                  60

Asn Gly Arg Phe Thr Ile Ser Leu Asp Asn Ala Gln Asn Thr Val Phe
 65                  70                  75                  80

Leu Gln Met Thr Ser Leu Thr Ala Ala Asp Thr Ala Thr Tyr Phe Cys
                    85                  90                  95

Ala Arg Asp Arg Gly Ala Tyr Ala Gly Ser Arg Gly Thr Arg Leu Asp
                100                 105                 110

Leu Trp Gly Gln Gly Thr Leu Val Thr Val Ser Ser
            115                 120

<210> SEQ ID NO 47
<211> LENGTH: 124
<212> TYPE: PRT
<213> ORGANISM: Homo sapiens
<220> FEATURE:

<400> SEQUENCE: 47

Gln Glu Gln Leu Met Glu Ser Gly Gly Gly Leu Val Thr Leu Gly Gly
                 5                  10                  15

Ser Leu Lys Leu Ser Cys Lys Ala Ser Gly Ile Asp Phe Ser His Tyr
                20                  25                  30

Gly Ile Ser Trp Val Arg Gln Ala Pro Gly Lys Gly Leu Glu Trp Ile
             35                  40                  45

Ala Tyr Ile Tyr Pro Asn Tyr Gly Ser Val Asp Tyr Ala Ser Trp Val
     50                  55                  60

Asn Gly Arg Phe Thr Ile Ser Leu Asp Asn Ala Gln Asn Thr Val Phe
 65                  70                  75                  80

Leu Gln Met Ile Ser Leu Thr Ala Ala Asp Thr Ala Thr Tyr Phe Cys
                    85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Ile Ser Ser
            115                 120

<210> SEQ ID NO 48
<211> LENGTH: 124
<212> TYPE: PRT
<213> ORGANISM: Homo sapiens
<220> FEATURE:

<400> SEQUENCE: 48

Gln Glu Gln Val Met Glu Ser Gly Gly Gly Leu Val Thr Leu Gly Gly
                  5                  10                  15
Ser Leu Lys Leu Ser Cys Lys Ala Ser Gly Ile Asp Phe Ser His Tyr
             20                  25                  30
Gly Ile Ser Trp Val Arg Gln Ala Pro Gly Lys Gly Leu Glu Trp Ile
         35                  40                  45
Ala Tyr Ile Tyr Pro Asn Tyr Gly Ser Val Asp Tyr Ala Ser Trp Val
     50                  55                  60
Asn Gly Arg Phe Thr Ile Ser Leu Asp Asn Ala Gln Asn Thr Val Phe
 65                  70                  75                  80
Leu Gln Met Ile Ser Leu Thr Ala Ala Asp Thr Ala Thr Tyr Phe Cys
                 85                  90                  95
Ala Arg Asp Arg Gly Tyr Tyr Ser Gly Ser Arg Gly Thr Arg Leu Asp
            100                 105                 110
Leu Trp Gly Gln Gly Thr Leu Val Thr Ile Ser Ser
        115                 120

<210> SEQ ID NO 49
<211> LENGTH: 124
<212> TYPE: PRT
<213> ORGANISM: Homo sapiens
<220> FEATURE:

<400> SEQUENCE: 49

Glu Val Gln Val Met Glu Ser Gly Gly Gly Leu Val Lys Pro Gly Gly
                  5                  10                  15
Ser Leu Arg Leu Ser Cys Ala Ala Ser Gly Phe Thr Phe Ser His Tyr
             20                  25                  30
Gly Ile Ser Trp Val Arg Gln Ala Pro Gly Lys Gly Leu Glu Trp Val
         35                  40                  45
Ser Tyr Ile Tyr Pro Asn Tyr Gly Ser Val Asp Tyr Ala Ser Ser Val
     50                  55                  60
Asn Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Asp Arg Gly Tyr Tyr Ser Gly Ser Arg Gly Thr Arg Leu Asp
            100                 105                 110
Leu Trp Gly Gln Gly Thr Leu Val Thr Val Ser Ser
        115                 120

<210> SEQ ID NO 50
<211> LENGTH: 124
<212> TYPE: PRT
<213> ORGANISM: Homo sapiens
<220> FEATURE:

<400> SEQUENCE: 50

Glu Val Gln Val Met Glu Ser Gly Gly Gly Leu Val Lys Pro Gly Gly
                  5                  10                  15
Ser Leu Arg Leu Ser Cys Ala Ala Ser Gly Ile Asp Phe Ser His Tyr

-continued

```
                20                  25                  30

Gly Ile Ser Trp Val Arg Gln Ala Pro Gly Lys Gly Leu Glu Trp Val
            35                  40                  45

Ser Tyr Ile Tyr Pro Asn Tyr Gly Ser Val Asp Tyr Ala Ser Ser Val
        50                  55                  60

Asn Gly Arg Phe Thr Ile Ser Phe Asp Asn Ala Gln Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120
```

<210> SEQ ID NO 51
<211> LENGTH: 124
<212> TYPE: PRT
<213> ORGANISM: Homo sapiens
<220> FEATURE:

<400> SEQUENCE: 51

```
Glu Val Gln Val Met Glu Ser Gly Gly Gly Leu Val Lys Pro Gly Gly
                5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
            35                  40                  45

Ser Tyr Ile Tyr Pro Asn Tyr Gly Ser Val Asp Tyr Ala Ser Ser Val
        50                  55                  60

Asn Gly Arg Phe Thr Ile Ser Leu Asp Asn Ala Gln Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120
```

<210> SEQ ID NO 52
<211> LENGTH: 124
<212> TYPE: PRT
<213> ORGANISM: Homo sapiens
<220> FEATURE:

<400> SEQUENCE: 52

```
Glu Val Gln Val Met Glu Ser Gly Gly Gly Leu Val Lys Pro Gly Gly
                5                   10                  15

Ser Leu Arg Leu Ser Cys Ala Ala Ser Gly Ile Asp Phe Ser His Tyr
            20                  25                  30

Gly Ile Ser Trp Val Arg Gln Ala Pro Gly Lys Gly Leu Glu Trp Val
            35                  40                  45

Ser Tyr Ile Tyr Pro Asn Tyr Gly Ser Val Asp Tyr Ala Ser Ser Val
        50                  55                  60

Asn Gly Arg Phe Thr Ile Ser Leu Asp Asn Ala Gln Asn Ser Leu Tyr
65                  70                  75                  80

Leu Gln Met Asn Ser Leu Arg Ala Glu Asp Thr Ala Val Tyr Tyr Cys
                85                  90                  95
```

-continued

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120

<210> SEQ ID NO 53
<211> LENGTH: 124
<212> TYPE: PRT
<213> ORGANISM: Homo sapiens
<220> FEATURE:

<400> SEQUENCE: 53

Glu Val Gln Val Met Glu Ser Gly Gly Leu Val Lys Pro Gly Gly
                 5                  10                  15

Ser Leu Arg Leu Ser Cys Ala Ala Ser Gly Ile Asp Phe Ser His Tyr
             20                  25                  30

Gly Ile Ser Trp Val Arg Gln Ala Pro Gly Lys Gly Leu Glu Trp Val
         35                  40                  45

Ser Tyr Ile Tyr Pro Asn Tyr Gly Ser Val Asp Tyr Ala Ser Ser Val
     50                  55                  60

Asn Gly Arg Phe Thr Ile Ser Leu Asp Asn Ala Gln Asn Ser Leu Tyr
65                  70                  75                  80

Leu Gln Met Asn Ser Leu Arg Ala Glu Asp Thr Ala Val Tyr Phe Cys
                 85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120

<210> SEQ ID NO 54
<211> LENGTH: 124
<212> TYPE: PRT
<213> ORGANISM: Homo sapiens
<220> FEATURE:

<400> SEQUENCE: 54

Glu Val Gln Val Met Glu Ser Gly Gly Leu Val Lys Pro Gly Gly
                 5                  10                  15

Ser Leu Arg Leu Ser Cys Ala Ala Ser Gly Phe Thr Phe Ser His Tyr
             20                  25                  30

Gly Ile Ser Trp Val Arg Gln Ala Pro Gly Lys Gly Leu Glu Trp Val
         35                  40                  45

Ser Tyr Ile Tyr Pro Asn Tyr Gly Ser Val Asp Tyr Ala Ser Ser Val
     50                  55                  60

Asn Gly Arg Phe Thr Ile Ser Phe Asp Asn Ala Gln Asn Ser Val Tyr
65                  70                  75                  80

Leu Gln Met Asn Ser Leu Arg Ala Glu Asp Thr Ala Val Tyr Tyr Cys
                 85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120

<210> SEQ ID NO 55
<211> LENGTH: 124
<212> TYPE: PRT
<213> ORGANISM: Homo sapiens
<220> FEATURE:

<400> SEQUENCE: 55

Glu Val Gln Val Met Glu Ser Gly Gly Gly Leu Val Lys Pro Gly Gly
1               5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Val Asp Tyr Ala Ser Ser Val
    50                  55                  60

Asn Gly Arg Phe Thr Ile Ser Leu Asp Asn Ala Gln Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 56
<211> LENGTH: 124
<212> TYPE: PRT
<213> ORGANISM: Homo sapiens
<220> FEATURE:

<400> SEQUENCE: 56

Glu Val Gln Val Met Glu Ser Gly Gly Gly Leu Val Lys Pro Gly Gly
1               5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Val Asp Tyr Ala Ser Ser Val
    50                  55                  60

Asn Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 57
<211> LENGTH: 124
<212> TYPE: PRT
<213> ORGANISM: Homo sapiens
<220> FEATURE:

<400> SEQUENCE: 57

Glu Val Gln Val Met Glu Ser Gly Gly Gly Leu Val Lys Pro Gly Gly
1               5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Val Asp Tyr Ala Ser Ser Val

```
            50                  55                  60
Asn Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Phe Cys
                 85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120

<210> SEQ ID NO 58
<211> LENGTH: 124
<212> TYPE: PRT
<213> ORGANISM: Homo sapiens
<220> FEATURE:

<400> SEQUENCE: 58

Glu Val Gln Val Met Glu Ser Gly Gly Leu Val Lys Pro Gly Gly
                  5                  10                  15

Ser Leu Arg Leu Ser Cys Ala Ala Ser Gly Ile Gly Phe Ser His Tyr
                 20                  25                  30

Gly Ile Ser Trp Val Arg Gln Ala Pro Gly Lys Gly Leu Glu Trp Val
             35                  40                  45

Ser Tyr Ile Tyr Pro Asn Tyr Gly Ser Val Asp Tyr Ala Ser Ser Val
         50                  55                  60

Asn Gly Arg Phe Thr Ile Ser Arg Asp Asn Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120

<210> SEQ ID NO 59
<211> LENGTH: 124
<212> TYPE: PRT
<213> ORGANISM: Homo sapiens
<220> FEATURE:

<400> SEQUENCE: 59

Glu Val Gln Val Met Glu Ser Gly Gly Leu Val Lys Pro Gly Gly
                  5                  10                  15

Ser Leu Arg Leu Ser Cys Ala Ala Ser Gly Ile Gly Phe Ser His Tyr
                 20                  25                  30

Gly Ile Ser Trp Val Arg Gln Ala Pro Gly Lys Gly Leu Glu Trp Val
             35                  40                  45

Ser Tyr Ile Tyr Pro Asn Tyr Gly Ser Val Asp Tyr Ala Ser Ser Val
         50                  55                  60

Asn Gly Arg Phe Thr Ile Ser Arg Asp Asn Ala Lys Asn Ser Val Tyr
 65                  70                  75                  80

Leu Gln Met Asn Ser Leu Arg Ala Glu Asp Thr Ala Val Tyr Phe Cys
                 85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120
```

<210> SEQ ID NO 60
<211> LENGTH: 124
<212> TYPE: PRT
<213> ORGANISM: Homo sapiens
<220> FEATURE:

<400> SEQUENCE: 60

Glu Val Gln Val Met Glu Ser Gly Gly Gly Leu Val Lys Pro Gly Gly
 1               5                  10                  15
Ser Leu Arg Leu Ser Cys Ala Ala Ser Gly Ile Gly Phe Ser His Tyr
            20                  25                  30
Gly Ile Ser Trp Val Arg Gln Ala Pro Gly Lys Gly Leu Glu Trp Val
        35                  40                  45
Ser Tyr Ile Tyr Pro Asn Tyr Gly Ser Val Asp Tyr Ala Ser Ser Val
    50                  55                  60
Asn Gly Arg Phe Thr Ile Ser Leu Asp Asn Ala Gln Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Gly Tyr Tyr Ser Gly Ser Arg Gly Thr Arg Leu Asp
            100                 105                 110
Leu Trp Gly Gln Gly Thr Leu Val Thr Val Ser Ser
        115                 120

<210> SEQ ID NO 61
<211> LENGTH: 124
<212> TYPE: PRT
<213> ORGANISM: Homo sapiens
<220> FEATURE:

<400> SEQUENCE: 61

Glu Val Gln Val Met Glu Ser Gly Gly Gly Leu Val Lys Pro Gly Gly
 1               5                  10                  15
Ser Leu Arg Leu Ser Cys Ala Ala Ser Gly Ile Gly Phe Ser His Tyr
            20                  25                  30
Gly Ile Ser Trp Val Arg Gln Ala Pro Gly Lys Gly Leu Glu Trp Val
        35                  40                  45
Ser Tyr Ile Tyr Pro Asn Tyr Gly Ser Val Asp Tyr Ala Ser Ser Val
    50                  55                  60
Asn Gly Arg Phe Thr Ile Ser Leu Asp Asn Ala Gln Asn Ser Leu Tyr
65                  70                  75                  80
Leu Gln Met Asn Ser Leu Arg Ala Glu Asp Thr Ala Val Tyr Phe Cys
                85                  90                  95
Ala Arg Asp Arg Gly Tyr Tyr Ser Gly Ser Arg Gly Thr Arg Leu Asp
            100                 105                 110
Leu Trp Gly Gln Gly Thr Leu Val Thr Val Ser Ser
        115                 120

<210> SEQ ID NO 62
<211> LENGTH: 124
<212> TYPE: PRT
<213> ORGANISM: Homo sapiens
<220> FEATURE:

<400> SEQUENCE: 62

Glu Val Gln Val Met Glu Ser Gly Gly Gly Leu Val Lys Pro Gly Gly
 1               5                  10                  15

```
Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
            35                  40                  45

Ser Tyr Ile Tyr Pro Asn Tyr Gly Ser Val Asp Tyr Ala Ser Ser Val
        50                  55                  60

Asn Gly Arg Phe Thr Ile Ser Leu Asp Asn Ala Gln Asn Ser Val Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120
```

<210> SEQ ID NO 63
<211> LENGTH: 124
<212> TYPE: PRT
<213> ORGANISM: Homo sapiens
<220> FEATURE:

<400> SEQUENCE: 63

```
Glu Val Gln Val Met Glu Ser Gly Gly Gly Leu Val Lys Pro Gly Gly
                5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
            35                  40                  45

Ser Tyr Ile Tyr Pro Asn Tyr Gly Ser Val Asp Tyr Ala Ser Ser Val
        50                  55                  60

Asn Gly Arg Phe Thr Ile Ser Leu Asp Asn Ala Gln Asn Ser Val Tyr
65                  70                  75                  80

Leu Gln Met Asn Ser Leu Arg Ala Glu Asp Thr Ala Val Tyr Phe Cys
                85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
            115                 120
```

<210> SEQ ID NO 64
<211> LENGTH: 124
<212> TYPE: PRT
<213> ORGANISM: Homo sapiens
<220> FEATURE:

<400> SEQUENCE: 64

```
Glu Val Gln Val Met Glu Ser Gly Gly Gly Leu Val Lys Pro Gly Gly
                5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
            35                  40                  45

Ser Tyr Ile Tyr Pro Asn Tyr Gly Ser Val Asp Tyr Ala Ser Ser Val
        50                  55                  60

Asn Gly Arg Phe Thr Ile Ser Asp Asn Ala Gln Asn Ser Leu Tyr
65                  70                  75                  80

Leu Gln Met Asn Ser Leu Arg Ala Glu Asp Thr Ala Val Tyr Tyr Cys
```

-continued

```
                85                  90                  95
Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
        115                 120
```

<210> SEQ ID NO 65
<211> LENGTH: 124
<212> TYPE: PRT
<213> ORGANISM: Homo sapiens
<220> FEATURE:

<400> SEQUENCE: 65

```
Glu Val Gln Val Met Glu Ser Gly Gly Gly Leu Val Lys Pro Gly Gly
                5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Val Asp Tyr Ala Ser Ser Val
    50                  55                  60

Asn Gly Arg Phe Thr Ile Ser Ser Asp Asn Ala Gln Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
        115                 120
```

<210> SEQ ID NO 66
<211> LENGTH: 124
<212> TYPE: PRT
<213> ORGANISM: Homo sapiens
<220> FEATURE:

<400> SEQUENCE: 66

```
Glu Val Gln Val Met Glu Ser Gly Gly Gly Leu Val Lys Pro Gly Gly
                5                   10                  15

Ser Leu Arg Leu Ser Cys Ala Ala Ser Gly Ile Gly Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Val Asp Tyr Ala Ser Ser Val
    50                  55                  60

Asn Gly Arg Phe Thr Ile Ser Ser Asp Asn Ala Gln Asn Ser Val Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Ser Gly Ser Arg Gly Thr Arg Leu Asp
                100                 105                 110

Leu Trp Gly Gln Gly Thr Leu Val Thr Val Ser Ser
        115                 120
```

<210> SEQ ID NO 67
<211> LENGTH: 124
<212> TYPE: PRT
<213> ORGANISM: Homo sapiens

```
<220> FEATURE:

<400> SEQUENCE: 67

Glu Val Gln Val Met Glu Ser Gly Gly Gly Leu Val Lys Pro Gly Gly
                  5                  10                  15

Ser Leu Arg Leu Ser Cys Ala Ala Ser Gly Ile Gly Phe Ser His Tyr
             20                  25                  30

Gly Ile Ser Trp Val Arg Gln Ala Pro Gly Lys Gly Leu Glu Trp Val
         35                  40                  45

Ser Tyr Ile Tyr Pro Asn Tyr Gly Ser Val Asp Tyr Ala Ser Ser Val
    50                  55                  60

Asn Gly Arg Phe Thr Ile Ser Ser Asp Asn Ala Gln Asn Ser Val Tyr
65                  70                  75                  80

Leu Gln Met Asn Ser Leu Arg Ala Glu Asp Thr Ala Val Tyr Phe Cys
                 85                  90                  95

Ala Arg Asp Arg Gly Tyr Tyr Ser Ser Arg Gly Thr Arg Leu Asp
                100                 105                 110

Leu Trp Gly Gln Gly Thr Leu Val Thr Val Ser Ser
            115                 120

<210> SEQ ID NO 68
<211> LENGTH: 11
<212> TYPE: PRT
<213> ORGANISM: Homo sapiens
<220> FEATURE:

<400> SEQUENCE: 68

Leu Ala Ser Glu Phe Leu Phe Asn Gly Val Ser
                  5                  10

<210> SEQ ID NO 69
<211> LENGTH: 11
<212> TYPE: PRT
<213> ORGANISM: Homo sapiens
<220> FEATURE:

<400> SEQUENCE: 69

Leu Ala Ser Asp Phe Leu Phe Asn Gly Val Ser
                  5                  10

<210> SEQ ID NO 70
<211> LENGTH: 7
<212> TYPE: PRT
<213> ORGANISM: Homo sapiens
<220> FEATURE:

<400> SEQUENCE: 70

Gly Ala Ser Asn Leu Glu Ser
                  5

<210> SEQ ID NO 71
<211> LENGTH: 7
<212> TYPE: PRT
<213> ORGANISM: Homo sapiens
<220> FEATURE:

<400> SEQUENCE: 71

Gly Ala Ser Asp Leu Glu Thr
                  5

<210> SEQ ID NO 72
<211> LENGTH: 11
```

```
<212> TYPE: PRT
<213> ORGANISM: Homo sapiens
<220> FEATURE:

<400> SEQUENCE: 72

Leu Gly Gly Tyr Ser Gly Ser Ser Gly Leu Thr
                 5                   10

<210> SEQ ID NO 73
<211> LENGTH: 11
<212> TYPE: PRT
<213> ORGANISM: Homo sapiens
<220> FEATURE:

<400> SEQUENCE: 73

Leu Gly Gly Tyr Ser Gly Ser Ala Gly Leu Thr
                 5                   10

<210> SEQ ID NO 74
<211> LENGTH: 5
<212> TYPE: PRT
<213> ORGANISM: Homo sapiens
<220> FEATURE:

<400> SEQUENCE: 74

His Tyr Gly Ile Ser
                 5

<210> SEQ ID NO 75
<211> LENGTH: 5
<212> TYPE: PRT
<213> ORGANISM: Homo sapiens
<220> FEATURE:

<400> SEQUENCE: 75

Asn Asn Gly Ile Ser
                 5

<210> SEQ ID NO 76
<211> LENGTH: 17
<212> TYPE: PRT
<213> ORGANISM: Homo sapiens
<220> FEATURE:

<400> SEQUENCE: 76

Tyr Ile Tyr Pro Asn Tyr Gly Ser Val Asp Tyr Ala Ser Ser Val Asn
                 5                   10                  15
Gly

<210> SEQ ID NO 77
<211> LENGTH: 17
<212> TYPE: PRT
<213> ORGANISM: Homo sapiens
<220> FEATURE:

<400> SEQUENCE: 77

Tyr Ile Tyr Pro Asn Tyr Gly Ser Val Asp Tyr Ala Ser Trp Val Asn
                 5                   10                  15
Gly

<210> SEQ ID NO 78
<211> LENGTH: 17
<212> TYPE: PRT
<213> ORGANISM: Homo sapiens
<220> FEATURE:
```

```
<400> SEQUENCE: 78

Tyr Ile Tyr Pro Asp Tyr Gly Ser Thr Asp Tyr Ala Ser Trp Val Asn
                5                   10                  15
Gly

<210> SEQ ID NO 79
<211> LENGTH: 15
<212> TYPE: PRT
<213> ORGANISM: Homo sapiens
<220> FEATURE:

<400> SEQUENCE: 79

Asp Arg Gly Tyr Tyr Ser Gly Ser Arg Gly Thr Arg Leu Asp Leu
                5                   10                  15

<210> SEQ ID NO 80
<211> LENGTH: 15
<212> TYPE: PRT
<213> ORGANISM: Homo sapiens
<220> FEATURE:

<400> SEQUENCE: 80

Asp Arg Gly Ala Tyr Ala Gly Ser Arg Gly Thr Arg Leu Asp Leu
                5                   10                  15

<210> SEQ ID NO 81
<211> LENGTH: 23
<212> TYPE: PRT
<213> ORGANISM: Homo sapiens
<220> FEATURE:

<400> SEQUENCE: 81

Glu Leu Gln Met Thr Gln Ser Pro Ser Ser Leu Ser Ala Ser Val Gly
                5                   10                  15
Asp Arg Val Thr Ile Thr Cys
            20

<210> SEQ ID NO 82
<211> LENGTH: 23
<212> TYPE: PRT
<213> ORGANISM: Homo sapiens
<220> FEATURE:

<400> SEQUENCE: 82

Glu Phe Asp Met Thr Gln Thr Pro Pro Ser Leu Ser Ala Ser Val Gly
                5                   10                  15
Glu Thr Val Arg Ile Arg Cys
            20

<210> SEQ ID NO 83
<211> LENGTH: 23
<212> TYPE: PRT
<213> ORGANISM: Homo sapiens
<220> FEATURE:

<400> SEQUENCE: 83

Glu Leu Val Met Thr Gln Thr Pro Pro Ser Leu Ser Ala Ser Val Gly
                5                   10                  15
Glu Thr Val Arg Ile Arg Cys
            20

<210> SEQ ID NO 84
```

```
<211> LENGTH: 23
<212> TYPE: PRT
<213> ORGANISM: Homo sapiens
<220> FEATURE:

<400> SEQUENCE: 84

Glu Leu Val Leu Thr Gln Thr Pro Ser Leu Ser Pro Ser Val Gly
                 5                  10                  15

Glu Thr Val Arg Ile Arg Cys
            20

<210> SEQ ID NO 85
<211> LENGTH: 15
<212> TYPE: PRT
<213> ORGANISM: Homo sapiens
<220> FEATURE:

<400> SEQUENCE: 85

Trp Tyr Gln Gln Lys Pro Gly Lys Ala Pro Lys Leu Leu Ile Tyr
                 5                  10                  15

<210> SEQ ID NO 86
<211> LENGTH: 15
<212> TYPE: PRT
<213> ORGANISM: Homo sapiens
<220> FEATURE:

<400> SEQUENCE: 86

Trp Tyr Gln Gln Lys Pro Gly Lys Ala Pro Lys Leu Leu Ile Tyr
                 5                  10                  15

<210> SEQ ID NO 87
<211> LENGTH: 15
<212> TYPE: PRT
<213> ORGANISM: Homo sapiens
<220> FEATURE:

<400> SEQUENCE: 87

Trp Tyr Gln Gln Lys Pro Gly Lys Val Pro Lys Phe Leu Ile Tyr
                 5                  10                  15

<210> SEQ ID NO 88
<211> LENGTH: 15
<212> TYPE: PRT
<213> ORGANISM: Homo sapiens
<220> FEATURE:

<400> SEQUENCE: 88

Trp Tyr Gln Gln Lys Pro Gly Lys Ala Pro Lys Phe Leu Ile Tyr
                 5                  10                  15

<210> SEQ ID NO 89
<211> LENGTH: 15
<212> TYPE: PRT
<213> ORGANISM: Homo sapiens
<220> FEATURE:

<400> SEQUENCE: 89

Trp Tyr Gln Gln Lys Pro Gly Lys Val Pro Lys Leu Leu Ile Tyr
                 5                  10                  15

<210> SEQ ID NO 90
<211> LENGTH: 15
<212> TYPE: PRT
<213> ORGANISM: Homo sapiens
<220> FEATURE:
```

<400> SEQUENCE: 90

Trp Tyr Gln Gln Lys Pro Gly Lys Pro Pro Lys Phe Leu Ile Ser
                5                   10                  15

<210> SEQ ID NO 91
<211> LENGTH: 15
<212> TYPE: PRT
<213> ORGANISM: Homo sapiens
<220> FEATURE:

<400> SEQUENCE: 91

Trp Tyr Gln Gln Lys Pro Glu Lys Pro Pro Thr Leu Leu Ile Ser
                5                   10                  15

<210> SEQ ID NO 92
<211> LENGTH: 32
<212> TYPE: PRT
<213> ORGANISM: Homo sapiens
<220> FEATURE:

<400> SEQUENCE: 92

Gly Val Pro Ser Arg Phe Ser Gly Ser Gly Ser Gly Thr Asp Phe Thr
                5                   10                  15

Leu Thr Ile Ser Ser Leu Gln Pro Glu Asp Val Ala Thr Tyr Tyr Cys
            20                  25                  30

<210> SEQ ID NO 93
<211> LENGTH: 32
<212> TYPE: PRT
<213> ORGANISM: Homo sapiens
<220> FEATURE:

<400> SEQUENCE: 93

Gly Val Pro Ser Arg Phe Ser Gly Ser Gly Ser Gly Thr Asp Tyr Thr
                5                   10                  15

Leu Thr Ile Ser Ser Leu Gln Pro Glu Asp Val Ala Thr Tyr Tyr Cys
            20                  25                  30

<210> SEQ ID NO 94
<211> LENGTH: 32
<212> TYPE: PRT
<213> ORGANISM: Homo sapiens
<220> FEATURE:

<400> SEQUENCE: 94

Gly Val Pro Ser Arg Phe Ser Gly Ser Gly Ser Gly Thr Asp Phe Thr
                5                   10                  15

Leu Thr Ile Ser Ser Leu Gln Pro Glu Asp Val Ala Thr Tyr Tyr Cys
            20                  25                  30

<210> SEQ ID NO 95
<211> LENGTH: 32
<212> TYPE: PRT
<213> ORGANISM: Homo sapiens
<220> FEATURE:

<400> SEQUENCE: 95

Gly Val Pro Pro Arg Phe Ser Gly Ser Gly Ser Gly Thr Asp Tyr Thr
                5                   10                  15

Leu Thr Ile Gly Gly Val Gln Ala Glu Asp Val Ala Thr Tyr Tyr Cys
            20                  25                  30

-continued

<210> SEQ ID NO 96
<211> LENGTH: 32
<212> TYPE: PRT
<213> ORGANISM: Homo sapiens
<220> FEATURE:

<400> SEQUENCE: 96

Gly Val Pro Pro Arg Phe Ser Gly Ser Gly Ser Gly Thr Asp Tyr Thr
                 5                  10                  15
Leu Thr Ile Gly Gly Val Gln Ala Glu Asp Ala Ala Thr Tyr Tyr Cys
             20                  25                  30

<210> SEQ ID NO 97
<211> LENGTH: 10
<212> TYPE: PRT
<213> ORGANISM: Homo sapiens
<220> FEATURE:

<400> SEQUENCE: 97

Phe Gly Gly Gly Thr Lys Val Glu Ile Lys
                 5                  10

<210> SEQ ID NO 98
<211> LENGTH: 10
<212> TYPE: PRT
<213> ORGANISM: Homo sapiens
<220> FEATURE:

<400> SEQUENCE: 98

Phe Gly Ala Gly Thr Asn Val Glu Ile Lys
                 5                  10

<210> SEQ ID NO 99
<211> LENGTH: 30
<212> TYPE: PRT
<213> ORGANISM: Homo sapiens
<220> FEATURE:

<400> SEQUENCE: 99

Glu Val Gln Val Met Glu Ser Gly Gly Gly Leu Val Lys Pro Gly Gly
                 5                  10                  15
Ser Leu Arg Leu Ser Cys Ala Ala Ser Gly Phe Thr Phe Ser
             20                  25                  30

<210> SEQ ID NO 100
<211> LENGTH: 30
<212> TYPE: PRT
<213> ORGANISM: Homo sapiens
<220> FEATURE:

<400> SEQUENCE: 100

Glu Val Gln Val Met Glu Ser Gly Gly Gly Leu Val Lys Pro Gly Gly
                 5                  10                  15
Ser Leu Arg Leu Ser Cys Ala Ala Ser Gly Ile Asp Phe Ser
             20                  25                  30

<210> SEQ ID NO 101
<211> LENGTH: 30
<212> TYPE: PRT
<213> ORGANISM: Homo sapiens
<220> FEATURE:

<400> SEQUENCE: 101

Glu Val Gln Val Met Glu Ser Gly Gly Gly Leu Val Lys Pro Gly Gly
                 5                  10                  15

```
Ser Leu Arg Leu Ser Cys Ala Ala Ser Gly Ile Gly Phe Ser
            20                  25                  30

<210> SEQ ID NO 102
<211> LENGTH: 30
<212> TYPE: PRT
<213> ORGANISM: Homo sapiens
<220> FEATURE:

<400> SEQUENCE: 102

Gln Gln Gln Val Met Glu Ser Gly Gly Gly Leu Val Thr Leu Gly Gly
                5                   10                  15

Ser Leu Thr Leu Thr Cys Lys Ala Ser Gly Ile Asp Phe Ser
            20                  25                  30

<210> SEQ ID NO 103
<211> LENGTH: 30
<212> TYPE: PRT
<213> ORGANISM: Homo sapiens
<220> FEATURE:

<400> SEQUENCE: 103

Gln Glu Gln Leu Met Glu Ser Gly Gly Gly Leu Val Thr Leu Gly Gly
                5                   10                  15

Ser Leu Lys Leu Ser Cys Lys Ala Ser Gly Ile Asp Phe Ser
            20                  25                  30

<210> SEQ ID NO 104
<211> LENGTH: 30
<212> TYPE: PRT
<213> ORGANISM: Homo sapiens
<220> FEATURE:

<400> SEQUENCE: 104

Gln Glu Gln Val Met Glu Ser Gly Gly Gly Leu Val Thr Leu Gly Gly
                5                   10                  15

Ser Leu Lys Leu Ser Cys Lys Ala Ser Gly Ile Asp Phe Ser
            20                  25                  30

<210> SEQ ID NO 105
<211> LENGTH: 14
<212> TYPE: PRT
<213> ORGANISM: Homo sapiens
<220> FEATURE:

<400> SEQUENCE: 105

Trp Val Arg Gln Ala Pro Gly Lys Gly Leu Glu Trp Ile Leu
                5                   10

<210> SEQ ID NO 106
<211> LENGTH: 14
<212> TYPE: PRT
<213> ORGANISM: Homo sapiens
<220> FEATURE:

<400> SEQUENCE: 106

Trp Val Arg Gln Ala Pro Gly Lys Gly Leu Glu Trp Ile Ala
                5                   10

<210> SEQ ID NO 107
<211> LENGTH: 14
<212> TYPE: PRT
<213> ORGANISM: Homo sapiens
<220> FEATURE:
```

<400> SEQUENCE: 107

Trp Val Arg Gln Ala Pro Gly Lys Gly Leu Glu Trp Val Ser
                 5                  10

<210> SEQ ID NO 108
<211> LENGTH: 32
<212> TYPE: PRT
<213> ORGANISM: Homo sapiens
<220> FEATURE:

<400> SEQUENCE: 108

Arg Phe Thr Ile Ser Arg Asp Asn Ala Lys Asn Ser Leu Tyr Leu Gln
                 5                  10                  15

Met Asn Ser Leu Arg Ala Glu Asp Thr Ala Val Tyr Tyr Cys Ala Arg
             20                  25                  30

<210> SEQ ID NO 109
<211> LENGTH: 32
<212> TYPE: PRT
<213> ORGANISM: Homo sapiens
<220> FEATURE:

<400> SEQUENCE: 109

Arg Phe Thr Ile Ser Phe Asp Asn Ala Gln Asn Ser Leu Tyr Leu Gln
                 5                  10                  15

Met Asn Ser Leu Arg Ala Glu Asp Thr Ala Val Tyr Tyr Cys Ala Arg
             20                  25                  30

<210> SEQ ID NO 110
<211> LENGTH: 32
<212> TYPE: PRT
<213> ORGANISM: Homo sapiens
<220> FEATURE:

<400> SEQUENCE: 110

Arg Phe Thr Ile Ser Leu Asp Asn Ala Gln Asn Ser Leu Tyr Leu Gln
                 5                  10                  15

Met Asn Ser Leu Arg Ala Glu Asp Thr Ala Val Tyr Phe Cys Ala Arg
             20                  25                  30

<210> SEQ ID NO 111
<211> LENGTH: 32
<212> TYPE: PRT
<213> ORGANISM: Homo sapiens
<220> FEATURE:

<400> SEQUENCE: 111

Arg Phe Thr Ile Ser Leu Asp Asn Ala Gln Asn Ser Leu Tyr Leu Gln
                 5                  10                  15

Met Asn Ser Leu Arg Ala Glu Asp Thr Ala Val Tyr Tyr Cys Ala Arg
             20                  25                  30

<210> SEQ ID NO 112
<211> LENGTH: 32
<212> TYPE: PRT
<213> ORGANISM: Homo sapiens
<220> FEATURE:

<400> SEQUENCE: 112

Arg Phe Thr Ile Ser Phe Asp Asn Ala Gln Asn Ser Val Tyr Leu Gln
                 5                  10                  15

Met Asn Ser Leu Arg Ala Glu Asp Thr Ala Val Tyr Tyr Cys Ala Arg

<210> SEQ ID NO 113
<211> LENGTH: 32
<212> TYPE: PRT
<213> ORGANISM: Homo sapiens
<220> FEATURE:

<400> SEQUENCE: 113

Arg Phe Thr Ile Ser Arg Asp Asn Ala Lys Asn Ser Leu Tyr Leu Gln
                5                   10                  15
Met Asn Ser Leu Arg Ala Glu Asp Thr Ala Val Tyr Tyr Cys Ala Arg
            20                  25                  30

<210> SEQ ID NO 114
<211> LENGTH: 32
<212> TYPE: PRT
<213> ORGANISM: Homo sapiens
<220> FEATURE:

<400> SEQUENCE: 114

Arg Phe Thr Ile Ser Arg Asp Asn Ala Lys Asn Ser Leu Tyr Leu Gln
                5                   10                  15
Met Asn Ser Leu Arg Ala Glu Asp Thr Ala Val Tyr Phe Cys Ala Arg
            20                  25                  30

<210> SEQ ID NO 115
<211> LENGTH: 32
<212> TYPE: PRT
<213> ORGANISM: Homo sapiens
<220> FEATURE:

<400> SEQUENCE: 115

Arg Phe Thr Ile Ser Arg Asp Asn Ala Lys Asn Ser Val Tyr Leu Gln
                5                   10                  15
Met Asn Ser Leu Arg Ala Glu Asp Thr Ala Val Tyr Tyr Cys Ala Arg
            20                  25                  30

<210> SEQ ID NO 116
<211> LENGTH: 32
<212> TYPE: PRT
<213> ORGANISM: Homo sapiens
<220> FEATURE:

<400> SEQUENCE: 116

Arg Phe Thr Ile Ser Arg Asp Asn Ala Lys Asn Ser Val Tyr Leu Gln
                5                   10                  15
Met Asn Ser Leu Arg Ala Glu Asp Thr Ala Val Tyr Phe Cys Ala Arg
            20                  25                  30

<210> SEQ ID NO 117
<211> LENGTH: 32
<212> TYPE: PRT
<213> ORGANISM: Homo sapiens
<220> FEATURE:

<400> SEQUENCE: 117

Arg Phe Thr Ile Ser Leu Asp Asn Ala Gln Asn Ser Leu Tyr Leu Gln
                5                   10                  15
Met Asn Ser Leu Arg Ala Glu Asp Thr Ala Val Tyr Tyr Cys Ala Arg
            20                  25                  30

-continued

```
<210> SEQ ID NO 118
<211> LENGTH: 32
<212> TYPE: PRT
<213> ORGANISM: Homo sapiens
<220> FEATURE:

<400> SEQUENCE: 118

Arg Phe Thr Ile Ser Leu Asp Asn Ala Gln Asn Ser Leu Tyr Leu Gln
                 5                  10                  15
Met Asn Ser Leu Arg Ala Glu Asp Thr Ala Val Tyr Phe Cys Ala Arg
             20                  25                  30

<210> SEQ ID NO 119
<211> LENGTH: 32
<212> TYPE: PRT
<213> ORGANISM: Homo sapiens
<220> FEATURE:

<400> SEQUENCE: 119

Arg Phe Thr Ile Ser Leu Asp Asn Ala Gln Asn Ser Val Tyr Leu Gln
                 5                  10                  15
Met Asn Ser Leu Arg Ala Glu Asp Thr Ala Val Tyr Tyr Cys Ala Arg
             20                  25                  30

<210> SEQ ID NO 120
<211> LENGTH: 32
<212> TYPE: PRT
<213> ORGANISM: Homo sapiens
<220> FEATURE:

<400> SEQUENCE: 120

Arg Phe Thr Ile Ser Leu Asp Asn Ala Gln Asn Ser Val Tyr Leu Gln
                 5                  10                  15
Met Asn Ser Leu Arg Ala Glu Asp Thr Ala Val Tyr Phe Cys Ala Arg
             20                  25                  30

<210> SEQ ID NO 121
<211> LENGTH: 32
<212> TYPE: PRT
<213> ORGANISM: Homo sapiens
<220> FEATURE:

<400> SEQUENCE: 121

Arg Phe Thr Ile Ser Ser Asp Asn Ala Gln Asn Ser Leu Tyr Leu Gln
                 5                  10                  15
Met Asn Ser Leu Arg Ala Glu Asp Thr Ala Val Tyr Tyr Cys Ala Arg
             20                  25                  30

<210> SEQ ID NO 122
<211> LENGTH: 32
<212> TYPE: PRT
<213> ORGANISM: Homo sapiens
<220> FEATURE:

<400> SEQUENCE: 122

Arg Phe Thr Ile Ser Ser Asp Asn Ala Gln Asn Ser Leu Tyr Leu Gln
                 5                  10                  15
Met Asn Ser Leu Arg Ala Glu Asp Thr Ala Val Tyr Phe Cys Ala Arg
             20                  25                  30

<210> SEQ ID NO 123
<211> LENGTH: 32
<212> TYPE: PRT
<213> ORGANISM: Homo sapiens
```

<220> FEATURE:

<400> SEQUENCE: 123

Arg Phe Thr Ile Ser Ser Asp Asn Ala Gln Asn Ser Val Tyr Leu Gln
                 5                  10                  15
Met Asn Ser Leu Arg Ala Glu Asp Thr Ala Val Tyr Tyr Cys Ala Arg
             20                  25                  30

<210> SEQ ID NO 124
<211> LENGTH: 32
<212> TYPE: PRT
<213> ORGANISM: Homo sapiens
<220> FEATURE:

<400> SEQUENCE: 124

Arg Phe Thr Ile Ser Ser Asp Asn Ala Gln Asn Ser Val Tyr Leu Gln
                 5                  10                  15
Met Asn Ser Leu Arg Ala Glu Asp Thr Ala Val Tyr Phe Cys Ala Arg
             20                  25                  30

<210> SEQ ID NO 125
<211> LENGTH: 11
<212> TYPE: PRT
<213> ORGANISM: Homo sapiens
<220> FEATURE:

<400> SEQUENCE: 125

Trp Gly Gln Gly Thr Leu Val Thr Ile Ser Ser
                 5                  10

<210> SEQ ID NO 126
<211> LENGTH: 11
<212> TYPE: PRT
<213> ORGANISM: Homo sapiens
<220> FEATURE:

<400> SEQUENCE: 126

Trp Gly Gln Gly Thr Leu Val Thr Val Ser Ser
                 5                  10

<210> SEQ ID NO 127
<211> LENGTH: 43
<212> TYPE: DNA
<213> ORGANISM: Homo sapiens
<220> FEATURE:

<400> SEQUENCE: 127
gatctccctc catgaaccat catcatcatc atcattgact gca          43

<210> SEQ ID NO 128
<211> LENGTH: 35
<212> TYPE: DNA
<213> ORGANISM: Homo sapiens
<220> FEATURE:

<400> SEQUENCE: 128
gtcaatgatg atgatgatga tggttcatgg agga          35

<210> SEQ ID NO 129
<211> LENGTH: 10
<212> TYPE: PRT
<213> ORGANISM: Artificial sequence
<220> FEATURE:
<223> OTHER INFORMATION: Designed peptide to act as a histidine rich
      region.

-continued

```
<400> SEQUENCE: 129

Ser Pro Ser Met His His His His His
1               5                   10
```